US011471496B2

(12) United States Patent
Keck et al.

(10) Patent No.: US 11,471,496 B2
(45) Date of Patent: Oct. 18, 2022

(54) COMPOSITIONS AND METHODS FOR TREATING OR AMELIORATING COCAINE ADDICTION

(71) Applicants: ROWAN UNIVERSITY, Glassboro, NJ (US); THE REGENTS OF THE UNIVERSITY OF COLORADO, A BODY CORPORATE, Denver, CO (US)

(72) Inventors: Thomas M. Keck, Philadelphia, PA (US); Christopher A. Lowry, Boulder, CO (US)

(73) Assignees: Rowan University, Glassboro, NJ (US); The Regents of the University of Colorado, Denver, CO (US)

( * ) Notice: Subject to any disclaimer, the term of this patent is extended or adjusted under 35 U.S.C. 154(b) by 48 days.

(21) Appl. No.: 16/804,815

(22) Filed: Feb. 28, 2020

(65) Prior Publication Data
US 2020/0276248 A1 Sep. 3, 2020

Related U.S. Application Data

(60) Provisional application No. 62/812,100, filed on Feb. 28, 2019.

(51) Int. Cl.
*A61K 35/74* (2015.01)
*A61P 25/30* (2006.01)

(52) U.S. Cl.
CPC .............. *A61K 35/74* (2013.01); *A61P 25/30* (2018.01)

(58) Field of Classification Search
None
See application file for complete search history.

(56) References Cited

FOREIGN PATENT DOCUMENTS

WO    WO-2014045023 A1 * 3/2014    .............. A61P 25/20

OTHER PUBLICATIONS

Back et al. Addict Behav. Feb. 2006;31(2):351-4. doi: 10.1016/j.addbeh.2005.05.008. Epub Jun. 13, 2005.*
Brodnik et al. Neuropharmacology 125 (2017) 295-307.*
Savignac et al. Neurogastroenterol Motil (2014) 26, 1615-1627.*
Agüero , et al., "The maternal microbiota drives early postnatal innate immune development", Science, vol. 351, Issue 6279, Mar. 18, 2016, pp. 1296-1302.
Amoroso , et al., "Intranasal *Mycobacterium vaccae* administration prevents stress-induced aggravation of dextran sulfate sodium (DSS) colitis", Brain, Behavior, and Immunity, vol. 80, 2019, pp. 595-604.
Amoroso , et al., "Subcutaneous *Mycobacterium vaccae* promotes resilience in a mouse model of chronic psychosocial srress when administered prior to or during psychosocial stress", Brain, Behav-
ior, and Immunity, vol. 87, Jul. 2020, pp. 309-317.
Aronica , et al., "Inflammation in epilepsy: Clinical observations", Epilepsia, vol. 52, 2011, pp. 26-32.
Arrant , et al., "Use of the light/dark test for anxiety in adult and adolescent male rats", Behav Brain Res, vol. 256, 2013, pp. 119-127.
Banerjee , et al., "Abnormal emotional learning in a rat model of autism exposed to valproic acid in utero", Frontiers in Behavioral Neuroscience, vol. 8, Article 387, Nov. 12, 2014, pp. 1-13.
Bercum , et al., "Maternal Stress Combined with Terbutaline Leads to Comorbid Autistic-Like Behavior and Epilepsy in a Rat Model", J Neurosci, vol. 35, No. 48, Dec. 2, 2015, pp. 15894-15902.
Berg , et al., "Revised terminology and concepts for organization of seizures and epilepsies: Report of the ILAE Commission on Classification and Terminology, 2005-2009", Epilepsia, vol. 51, No. 4, 2010, pp. 676-685.
Besag , et al., "Epilepsy in patients with autism: links, risks and treatment challenges", Neuropsychiatr Dis Treat, vol. 14, 2017, pp. 1-10.
Bettelli , et al., "Induction and effector functions of TH17 cells", Nature, vol. 453, Jun. 19, 2008, pp. 1051-1057.
Bettelli , et al., "Reciprocal developmental pathways for the generation of pathogenic effector T H 17 and regulatory T cells", Nature, vol. 441(7090), May 11, 2006, pp. 235-238.
Bilbo , et al., "Beyond infection—Maternal immune activation by environmental factors, microglial development, and relevance for autism spectrum disorders", Exp Neurol, vol. 299, Part A, Jan. 2018, pp. 241-251.
Bowers , et al., "Preimmunization with a non-pathogenic bacterium *Mycobacterium vaccae* NCTC11659 prevents the development of cortical hyperarousal and PTSD-like sleep phenotype following sleep disruption plus acute stress in mice", Sleep, vol. 42, Suppl 1, 2019, pp. A94-95.
Bowers , et al., "Repeated sleep disruption in mice leads to persistent shifts in the fecal microbiome and metabolome", PLoS One, vol. 15, 2020, pp. e0229001.
Brooks-Kayal , "Epilepsy and autism spectrum disorders: Are there common developmental mechanisms?", Brain and Development, Special Section: Epilepsy in Autism Spectrum Disorders and Related Conditions, vol. 32, Issue 9, May 31, 2010, pp. 731-738.
Buckmaster , et al., "Network Properties of the Dentate Gyrus in Epileptic Rats With Hilar Neuron Loss and Granule Cell Axon Reorganization", J Neurophysiol, vol. 77, Issue 5, 1997, pp. 2685-2696.
Buffington , et al., "Microbial reconstitution reverses maternal diet-induced social and synaptic deficits in offspring", Cell, vol. 165, No. 7, Jun. 16, 2016, pp. 1762-1775.
Caccamise , et al., "Neurochemical mechanisms and neurocircuirty underlying the contribution of stress to cocaine seeking", J Neurochem, vol. 157, 2021, pp. 1697-1713.

(Continued)

*Primary Examiner* — Oluwatosin A Ogunbiyi
(74) *Attorney, Agent, or Firm* — Saul Ewing Arnstein & Lehr LLP; Domingos J. Silva; Dennis Ostrovsky

(57) ABSTRACT

The present invention provides compositions and methods for treating, ameliorating, and/or preventing cocaine addiction in a subject. Immunization by *M. vaccae* alters serotonin signaling in the brain, reducing stress- and anxiety-like responding in animal models of post-traumatic stress disorder and other anxiety disorders. In certain embodiments, the immunoregulatory, anti-stress, and anxiolytic effects of *M. vaccae* immunization reduces addiction- and relapse-like responding in models of cocaine addiction and alter the development of cocaine-induced neuroinflammation.

10 Claims, 11 Drawing Sheets

(56) References Cited

OTHER PUBLICATIONS

Chaidez, et al., "Gastrointestinal problems in children with autism, developmental delays or typical development", J Autism Dev Disord 44, May 2014, pp. 1117-1127.
Charil, et al., "Prenatal stress and brain development", Brain Res Rev, vol. 65, No. 1, Oct. 2010, pp. 56-79.
Choi, et al., "The maternal interleukin-17a pathway in mice promotes autism-like phenotypes in offspring", Sciences, vol. 351, Feb. 26, 2016, pp. 933-939.
Clarke, et al., "The prevalence of autistic spectrum disorder in children surveyed in a tertiary care epilepsy clinic", Epilepsia, vol. 46, No. 12, 2005, pp. 1970-1977.
Craig, et al., "How do you feel? Interoception: the sense of the physiological condition of the body", Nat Rev Neurosci, vol. 3, No. 8, 2002, pp. 655-666.
Day, et al., "Differential Pattern of c-fos mRNA in Rat Brain following Central and Systemic Administration of Interleukin-1-Beta: Implications for Mechanism of Action", Neuroendocrinology, vol. 63, No. 3, Mar. 1996, pp. 207-218.
De Boer, et al., "Defensive burying in rodents: ethology, neurobiology and psychopharmacology", Eur J Pharmacol, vol. 463 (1-3), Feb. 28, 2003, pp. 145-161.
De La Garza, II, et al., "Influence of Verbal Recall of a Recent Stress Experience on Anxiety and Desire for Cocaine in Non-Treatment Seeking, Cocaine-Addicted Volunteers", Am J Addictions, vol. 18, 2009, pp. 481-487.
Delpech, et al., "Early life stress perturbs the maturation of microglia in the developing hippocampus", Brain Behav Immun, vol. 57, Oct. 2016, pp. 79-93.
Depino, "Peripheral and central inflammation in autism spectrum disorders", Mol Cell Neurosci, vol. 53, 2013, pp. 69-76.
Desbonnet, et al., "Gut microbiota depletion from early adolescence in mice: Implications for brain and behaviour", Brain Behav Immun, vol. 48, Aug. 2015, pp. 165-173.
Dinan, et al., "Hypothalamic-Pituitary-Gut Axis Dysregulation in Irritable Bowel Syndrome: Plasma Cytokines as a Potential Biomarker?", Gastroenterology, vol. 130, No. 2, Feb. 2006, pp. 304-311.
Diz-Chaves, et al., "Prenatal stress causes alterations in the morphology of microglia and the inflammatory response of the hippocampus of adult female mice", J Neuroinflammation, vol. 9:71, 2012, pp. 1-10.
Dole, et al., "Maternal stress and preterm birth", Am J Epidemiol, vol. 157, No. 1, Jan. 1, 2003, pp. 14-24.
Dubé, et al., "Hyper-excitability and epilepsy generated by chronic early-life stress", Neurobiology of Stress, vol. 2, 2015, pp. 10-19.
Edmiston, et al., "Autoimmunity, Autoantibodies, and Autism Spectrum Disorder", Biol Psychiatry, vol. 81, No. 5, Mar. 1, 2017, pp. 383-390.
Entringer, et al., "Prenatal exposure to maternal psychosocial stress and HPA axis regulation in young adults", Horm Behav, vol. 55, No. 2, Feb. 2009, pp. 292-298.
File, et al., "Can Social Interaction Be Used to Measure Anxiety?", Br J Pharmac, vol. 62, 1978, pp. 19-24.
Fonken, et al., "*Mycobacterium vaccae* immunization protects aged rats from surgery-elicited neuroinflammation and cognitive dysfunction", Neurobiology of Aging, vol. 71, 2018, pp. 105-114.
Fonken, et al., "The Alarmin HMGB1 Mediates Age-Induced Neuroinflammatory Priming", J Neurosci, vol. 36, No. 30, Jul. 27, 2016, pp. 7946-7956.
Fox, et al., "Preimmunization with a heat-killed preparation of *Mycobacterium vaccae* enhances fear extinction in the fear-potentiated startle paradigm", Brain Behav Immun, vol. 66, Nov. 2017, pp. 70-84.
Frank, et al., "Chronic exposure to exogenous glucocorticoids primes microglia to pro-inflammatory stimuli and induces NLRP3 mRNA in the hippocampus", Psychoneuroendocrinology, vol. 40, Feb. 2014, pp. 191-200.
Frank, et al., "Could Probiotics Be Used to Mitigate Neuroinflammation?", ACS Chem Neurosci, vol. 10, 2019, pp. 13-15.
Frank, et al., "Immunization with *Mycobacterium vaccae* induces an anti-inflammatory milieu in the CNS: Attenuation of stress-induced microglial priming, alarmins and anxiety-like behavior", Brain Behav Immun, vol. 73, 2018, pp. 352-363.
Frank, et al., "Microglia serve as a neuroimmune substrate for stress-induced potentiation of CNS pro-inflammatory cytokine responses", Brain Behav Immun, vol. 21, No. 1, Jan. 2007, pp. 47-59.
Frank, et al., "Rapid isolation of highly enriched and quiescent microglia from adult rat hippocampus: Immunophenotypic and functional characteristics", J Neurosci Methods, vol. 151, No. 2, Mar. 15, 2006, pp. 121-130.
Fujita, et al., "Adrenergic agonists suppress the proliferation of microglia through $\beta 2$-adrenergic receptor", Neurosci Lett, vol. 242, No. 1, Feb. 6, 1998, pp. 37-40.
Furnari, et al., "Some of the people, some of the time: field evidence for associations and dissociations between stress and drug use", Psychopharmacology, vol. 232, 2015, pp. 3529-3537.
Gao, et al., "Common Mechanisms of Excitatory and Inhibitory Imbalance in Schizophrenia and Autism Spectrum Disorders", Curr Mol Med, vol. 15(2), 2015, pp. 146-167.
Ghacibeh, et al., "Interictal epileptiform activity and autism", Epilepsy Behav, vol. 47, Jun. 2015, pp. 158-162.
Gillberg, "The treatment of epilepsy in autism", J Autism Dev Disord, vol. 21, No. 1, Mar. 1991, pp. 61-77.
Glover, et al., "Prenatal stress and the programming of the HPA axis", Neurosci Biobehav Rev, vol. 35, No. 1, Sep. 2010, pp. 17-22.
Rodier, P., "Does treatment of premature labor with terbutaline increase the risk of autism spectrum disorders?", American Journal of Obstetrics and Gynecology, vol. 204, No. 2, 2011, pp. 91-94.
Rook, et al., "Hygiene and other early childhood influences on the subsequent function of the immune system", Brain Res, vol. 1617, 2015, pp. 47-62.
Rook, G.A., "Regulation of the immune system by biodiversity from the natural environment: An ecosystem service essential to health", PNAS, vol. 110, No. 46, 2013, pp. 18360-18367.
Roque, et al., "Maternal separation activates microglial cells and induces an inflammatory response in the hippocampus of male rat pups, independently of hypothalamic and peripheral cytokine levels", Brain, Behavior, and Immunity, vol. 55, 2016, pp. 39-48.
Sanders, et al., "Changes in postnatal norepinephrine alter alpha-2 adrenergic receptor development", Neuroscience, vol. 192, 2011, pp. 761-772.
Schmidt, et al., "Beta(2)-adrenergic receptors potentiate glucocorticoid receptor transactivation via G protein beta gamma-subunits and the phosphoinositide 3-kinase pathway", Mol Endocrinol, vol. 15, No. 4, 2001, pp. 553-564.
Sengupta, P., "The Laboratory Rat: Relating Its Age With Human's", Int J Prev Med, vol. 4, 2013, pp. 624-630.
Sgritta, et al., "Mechanisms Underlying Microbial-Mediated Changes in Social Behavior in Mouse Models of Autism Spectrum Disorder", Neuron 101, 2019, pp. 246-259.
Singletary, W.M., "An integrative model of autism spectrum disorder: ASD as a neurobiological disorder of experienced environmental deprivation, early life stress and allostatic overload", Neuropsychoanalysis, vol. 17, No. 2, 2015, pp. 81-119.
Slotkin, et al., "Anomalous regulation of $\beta$-adrenoceptor signaling in brain regions of the newborn rat", Brain Research, vol. 1077, No. 1, 2006, pp. 54-58.
Slotkin, et al., "Developmental neurotoxicity resulting from pharmacotherapy of preterm labor, modeled in vitro: Terbutaline and dexamethasone, separately and together", Toxicol, vol. 400-401, 2018, pp. 57-64.
Slotkin, et al., "Prenatal terbutaline exposure in the rat: selective effects on development of noradrenergic projections to cerebellum", Brain Res Bulletin, vol. 23, Nos. 4-5, 1989, pp. 263-265.
Slotkin, et al., "Terbutaline impairs the development of peripheral noradrenergic projections: Potential implications for autism spectrum disorders and pharmacotherapy of preterm labor", Neurotoxicol Teratol, vol. 36, 2013, pp. 91-96.
Slotkin, et al., "$\beta$-Adrenoceptor signaling in the developing brain: sensitization or desensitization in response to terbutaline", Dev Brain Res, vol. 131, No. 1-2, 2001, pp. 113-125.

(56) References Cited

OTHER PUBLICATIONS

Smith, et al., "Identification and characterization of a novel anti-inflammatory lipid isolated from *Mycobacterium vaccae*, a soil-derived bacterium with immunoregulatory and stress resilience properties", Psychopharmacology (Berl), vol. 236, No. 5, 2019, pp. 1653-1670.
Smith, et al., "Maternal Immune Activation Alters Fetal Brain Development through Interieukin-6", J Neurosci, vol. 27, No. 40, 2007, pp. 10695-10702.
Smith, et al., "Progression of convulsive and nonconvulsive seizures during epileptogenesis after pilocarpine-induced status epilepticus", J Neurophysiol, vol. 119, 2018, pp. 1818-1835.
Staley, et al., "Interictal Spikes and Epileptogenesis", Epilepsy Currents, vol. 6, No. 6, 2006, pp. 199-202.
Steffenburg, et al., "Autism spectrum disorders in children with active epilepsy and learning disability: comorbidity, pre- and perinatal background, and seizure characteristics", Developmental Medicine & Child Neurology, vol. 45, 2003, pp. 724-730.
Taylor, et al., "Spontaneous Recurrent Absence Seizure-like Events in Wild-Caught Rats", J Neurosci, vol. 39, No. 24, 2019, pp. 4829-4841.
Uddin, L.Q., "Salience processing and insular cortical function and dysfunction", Nature Reviews Neuroscience, vol. 16, 2014, pp. 55-61.
Uddin, et al., "The anterior insula in autism: Under-connected and under-examined", Neurosci Biobehav Rev, vol. 33, No. 8, 2009, pp. 1198-1203.
Ulrich-Lai, et al., "Neural Regulation of Endocrine and Autonomic Stress Responses", Nat Rev Neurosci, vol. 10, No. 6, 2009, pp. 397-409.
Van Bodegom, et al., "Modulation of the Hypothalamic-Pituitary-Adrenal Axis by Early Life Stress Exposure", Front Cell Neurosci, vol. 11, Article 87, 2017, pp. 1-33.
Van Campen, et al., "Early life stress in epilepsy: A seizure precipitant and risk factor for epileptogenesis", Epilepsy & Behavior, Special Issue: NEWroscience 2013, vol. 38, 2014, pp. 160-171.
Varcin, et al., "Prenatal maternal stress events and phenotypic outcomes in Autism Spectrum Disorder", Autism Res, vol. 10, No. 11, 2017, pp. 1866-1877.
Vezzani, et al., "The role of inflammation in epileptogenesis", Neuropharmacology, vol. 69, 2013, pp. 16-24.
Walf, et al., "The use of the elevated plus maze as an assay of anxiety-related behavior in rodents", Nat Protoc, vol. 2, No. 2,, 2007, pp. 322-328.
Washington, et al., "Cytokine-dependent bidirectional connection between impaired social behavior and susceptibility to seizures associated with maternal immune activation in mice", Epilepsy Behav, vol. 50, 2015, pp. 40-45.
Wei, et al., "Early-Life Stress Perturbs Key Cellular Programs in the Developing Mouse Hippocampus", Dev Neurosci, vol. 37, 2015, pp. 476-488.
White, et al., "Anxiety in Children and Adolescents with Autism Spectrum Disorders", Clin Psychol Rev, vol. 29, No. 3, 2009, pp. 216-229.
Witter, F.R., "Does treatment of premature labor with terbutaline increase the risk of autism spectrum disorders?", Am J Obstetrics & Gynecology, vol. 205, 2011, pp. 312.
Witter, et al., "utero beta 2 adrenergic agonist exposure and adverse neurophysiologic and behavioral outcomes", Am J Obstetrics and Gynecology, vol. 201, No. 6, 2009, pp. 553-559.
Wohr, et al., "Behavioural methods used in rodent models of autism spectrum disorders: Current standards and new developments", Behavioural Brain Research, vol. 251, 2013, pp. 5-17.
Wu, et al., "Microglia: Dynamic Mediators of Synapse Development and Plasticity", Trends Immunol, vol. 36, No. 10, 2015, pp. 605-613.
Zerrate, et al., "Neuroinflammation and Behavioral Abnormalities after Neonatal Terbutaline Treatment in Rats: Implications for Autism", J Pharmacol Exp Therapeutics, vol. 322, No. 1, 2007, pp. 16-22.
Zuany-Amorim, et al., "Suppression of airway eosinophilia by killed *Mycobacterium vaccae*-induced allergen-specific regulatory T-cells", Nature Medicine, vol. 8, No. 6, 2002, pp. 625-629.
Gogolla, et al., "Sensory Integration in Mouse Insular Cortex Reflects GABA Circuit Maturation", Neuron, vol. 83, No. 4, Aug. 20, 2014, pp. 894-905.
Gorka, et al., "Effect of chronic mild stress on circadian rhythms in the locomotor activity in rats", Pharmacol Biochem Behav, vol. 54, No. 1, May 1996, pp. 229-234.
Gröschel, et al., "Therapeutic vaccines for tuberculosis—A systematic review", Vaccine, vol. 32, No. 26, May 30, 2014, pp. 3162-3168.
Gumusoglu, et al., "The role of IL-6 in neurodevelopment after prenatal stress", Brain Behav Immun, vol. 65, Oct. 2017, pp. 274-283.
Gunn, et al., "The Endogenous Stress Hormone CRH Modulates Excitatory Transmission and Network Physiology in Hippocampus", Cerebral Cortex, vol. 27, Aug. 2017, pp. 4182-4198.
Gyoneva, et al., "Norepinephrine Modulates the Motility of Resting and Activated Microglia via Different Adrenergic Receptors", J Biol Chem, vol. 288, No. 21, May 24, 2013, pp. 15291-15302.
Haas, et al., "Short-term tocolytics for preterm delivery—current perspectives", Intl J Womens Health, vol. 6, 2014, pp. 343-349.
Harris, et al., "Glucocorticoids, prenatal stress and the programming of disease", Horm Behav, vol. 59, No. 3, Mar. 2011, pp. 279-289.
Hassell, Jr., et al., "Treatment with a heat-killed preparation of *Mycobacterium vaccae* after fear conditioning enhances fear extinction in the fear-potentiated startle paradigm", Brain Behav Immun, vol. 81, 2019, pp. 151-160.
Heo, et al., "IL-10 suppresses Th17 cells and promotes regulatory T cells in the CD4+ T cell population of rheumatoid arthritis patients", Immunol Lett, vol. 127, No. 2, Jan. 4, 2010, pp. 150-156.
Hollrigel, et al., "The pro-convulsant actions of corticotropin-releasing hormone in the hippocampus of infant rats", Neuroscience, vol. 84, No. 1, May 1998, pp. 71-79.
Holmes, et al., "Alterations in sociability and functional brain connectivity caused by early-life seizures are prevented by bumetanide", Neurobiol Dis, vol. 77, May 2015, pp. 204-219.
Hsiao, et al., "Activation of the Maternal Immune System Induces Endocrine Changes in the Placenta via IL-6", Brain Behav Immun, vol. 25, No. 4, May 2011, pp. 604-615.
Hsiao, et al., "Microbiota Modulate Behavioral and Physiological Abnormalities Associated with Neurodevelopmental Disorder", Cell, vol. 155, No. 7, Dec. 19, 2013, pp. 1451-1463.
Ivy, et al., "Dysfunctional nurturing behavior in rat dams with limited access to nesting material: a clinically relevant model for early-life stress", Neurosci, vol. 154, No. 3, Jun. 26, 2008, pp. 1132-1142.
Jesarevic, et al., "A novel role for maternal stress and microbial transmission in early life programming and neurodevelopment.", Neurobiol Stress, vol. 1, 2014, pp. 81-88.
Johnson, et al., "arly life stress perturbs the function of microglia in the developing rodent brain: New insights and future challenges", Brain, Behavior, and Immunity, vol. 69, 2018, pp. 18-27.
Kim, et al., "A postnatal peak in microglial development in the mouse hippocampus is correlated with heightened sensitivity to seizure triggers", Brain and Behavior, vol. 5, No. 12, 2015, pp. e00403 (14 pgs).
Kim, et al., "Absence of seizures despite high prevalence of epileptiform EEG abnormalities in children with autism monitored in a tertiary care center", Epilepsia, vol. 47, No. 2, 2006, pp. 394-398.
Kinney, et al., "Prenatal stress and risk for autism", Neurosci Biobehav Rev, vol. 32, No. 8, Oct. 2008, pp. 1519-1532.
Lan, et al., "Modulators of microglial activation and polarization after intracerebral haemorrhage", Nat Rev Neurol, vol. 13, No. 7, Jul. 2017, pp. 420-433.
Langgartner, et al., "Old Friends, immunoregulation, and stress resilience", Pflugers Arch, E J Phytsiol, vol. 471, 2019, pp. 237-269.
Lewine, et al., "Magnetoencephalographic patterns of epileptiform activity in children with regressive autism spectrum disorders", Pediatrics, vol. 104 (3 part 2), 1999, pp. 405-418.

(56) References Cited

OTHER PUBLICATIONS

Lothman, et al., "The dentate gyrus as a control point for seizures in the hippocampus and beyond", Epilepsy Res Suppl, vol. 76, 1992, pp. 301-313.

Loupy, et al., "Evidence that preimmunization with a heat-killed preparation of Mycobacterium vaccae reduces corticotropin-releasing hormone mRNA expression in the extended amygdala in a fear-potentiated startle paradigm", Brain Behav Immun, vol. 77, 2019, pp. 127-140.

Lowry, et al., "The Microbiota, Immunoregulation, and Mental Health: Implications for Public Health", Curr Environ Health Rep, vol. 3, No. 3, 2016, pp. 270-286.

Maguire, et al., "Seizures, and Hypothalamic-Pituitary-Adrenal Axis Targets for the Treatment of Epilepsy", Epilepsy Behav, vol. 26, No. 3, 2013, pp. 352-362.

Mazefsky, et al., "The Role of Emotion Regulation in Autism Spectrum Disorder RH: Emotion Regulation in ASD", J Am Acad Child Adolesc Psychiatry, vol. 52, No. 7, 2013, pp. 679-688.

McEwen, B., "A key role for allostatic overload in ASD and other disorders. Commentary on "An integrative model of autism spectrum disorder: ASD as a neurobiological disorder of experienced environmental deprivation, early life stress, and allostatic overload" by Willi", Neuropsychoanalysis, vol. 18, No. 1, 2016, pp. 9-14.

McEwen, B., "Stress, adaptation, and disease: Allostasis and allostatic load", Ann NY Acad Sci, vol. 840, No. 1, 1998, pp. 33-44.

Mehta, et al., "Prolactin and cortisol levels in seizure disorder", J Assoc Physicians India, vol. 42, No. 9, 1994, pp. 709-712.

Meltzer, et al., "The Role of the Immune System in Autism Spectrum Disorder", Neuropsychopharmacology Reviews, vol. 42, 2017, pp. 284-298.

Molet, et al., "Naturalistic rodent models of chronic early-life stress", Dev Psychobiol, vol. 56, No. 8, 2014, pp. 1675-1688.

Nandan, et al., "Support vector machines for seizure detection in an animal model of chronic epilepsy", J Neural Eng, vol. 7, 2010, pp. 036001 (12 pgs).

Nikodemova, et al., "Microglial numbers attain adult levels after undergoing a rapid decrease in cell number in the third postnatal week", J Neuroimmunol, vol. 278, 2015, pp. 280-288.

Nir, et al., "Brief report: Circadian melatonin, thyroid-stimulating hormone, prolactin, and cortisol levels in serum of young adults with autism", J Autism Dev Disord, vol. 25, 1995, pp. 641-654.

Noronha, et al., "Association of high-fat diet with neuroinflammation, anxiety-like defensive behavioral responses, and altered thermoregulatory responses in male rats", Brain Behav Immun, vol. 80, 2019, pp. 500-511.

Orru, et al., "Using Support Vector Machine to identify imaging biomarkers of neurological and psychiatric disease: A critical review", Neuroscience & Biobehavioral Reviews, vol. 36, No. 4, 2012, pp. 1140-1152.

Paolicelli, et al., "Function and Dysfunction of Microglia during Brain Development: Consequences for Synapses and Neural Circuits", Front Synaptic Neurosci, vol. 9, Article 9, 2017, 3 pages.

Paolicelli, et al., "Synaptic Pruning by Microglia is Necessary for Normal Brain Development", Science, vol. 333, 2011, pp. 1456-1458.

Patterson, P.H., "Modeling autistic features in animals", Pediatr Res, vol. 69, No. 5, Pt. 2, 2011, pp. 34R-40R.

Perna, et al., "Terbutaline and associated risks for neurodevelopmental disorders", Child Development Research, vol. 2014, Article ID 358608, 2014, 6 pages.

Picci, et al., "A Two-Hit Model of Autism: Adolescence as the Second Hit", Clin Psychol Sci, vol. 3, No. 3, 2015, pp. 349-371.

Pineda, et al., "Maternal immune activation promotes hippocampal kindling epileptogenesis in mice", Ann Neurol, vol. 74, No. 1, 2013, pp. 11-19.

Racine, R.J., "Modification of seizure activity by electrical stimulation: II. Motor seizure", Electroenceph Clin Neurophysiol, vol. 32, 1972, pp. 281-294.

Reber, et al., "Immunization with a heat-killed preparation of the environmental bacterium Mycobacterium vaccae promotes stress resilience in mice", PNAS, vol. 113, 2016, pp. E3130-E3139.

Rhodes, "Terbutaline Is a Developmental Neurotoxicant: Effects on Neuroproteins and Morphology in Cerebellum, Hippocampus, and Somatosensory Cortex", J Pharmacol Exp Ther, vol. 308, No. 2, 2004, pp. 529-537.

Rice, et al., "A Novel Mouse Model for Acute and Long-Lasting Consequences of Early Life Stress", Endocrinology, vol. 149, No. 10, 2008, pp. 4892-4900.

Rice, et al., "Evaluating Changes in the Prevalence of the Autism Spectrum Disorders (ASDs)", Public Health Rev, vol. 34, No. 2, 2012, pp. 1-22.

Rodgers, et al., "Auditory, Somatosensory, and Multisensory Insular Cortex in the Rat", Cereb Cortex, vol. 18, 2008, pp. 2941-2951.

\* cited by examiner

FIG. 3
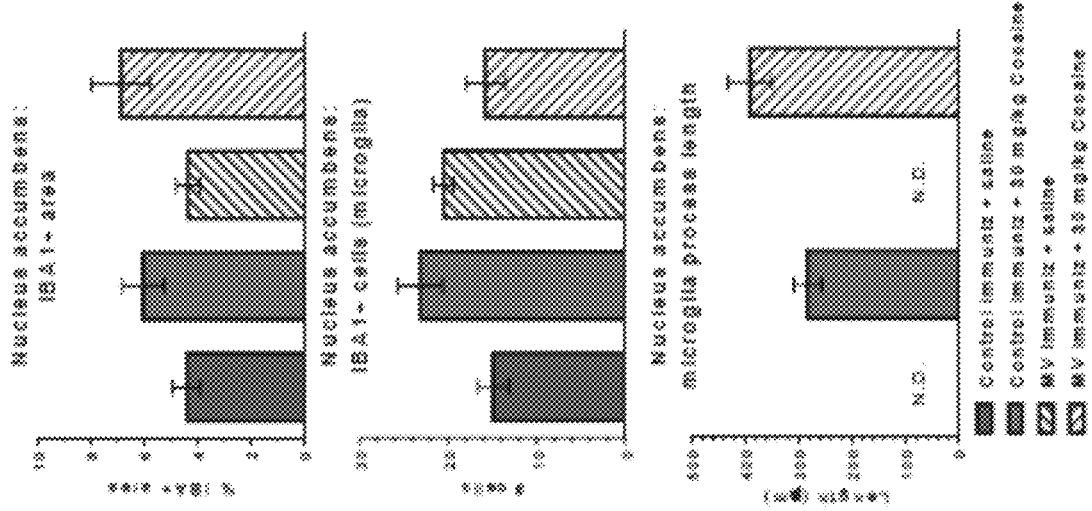
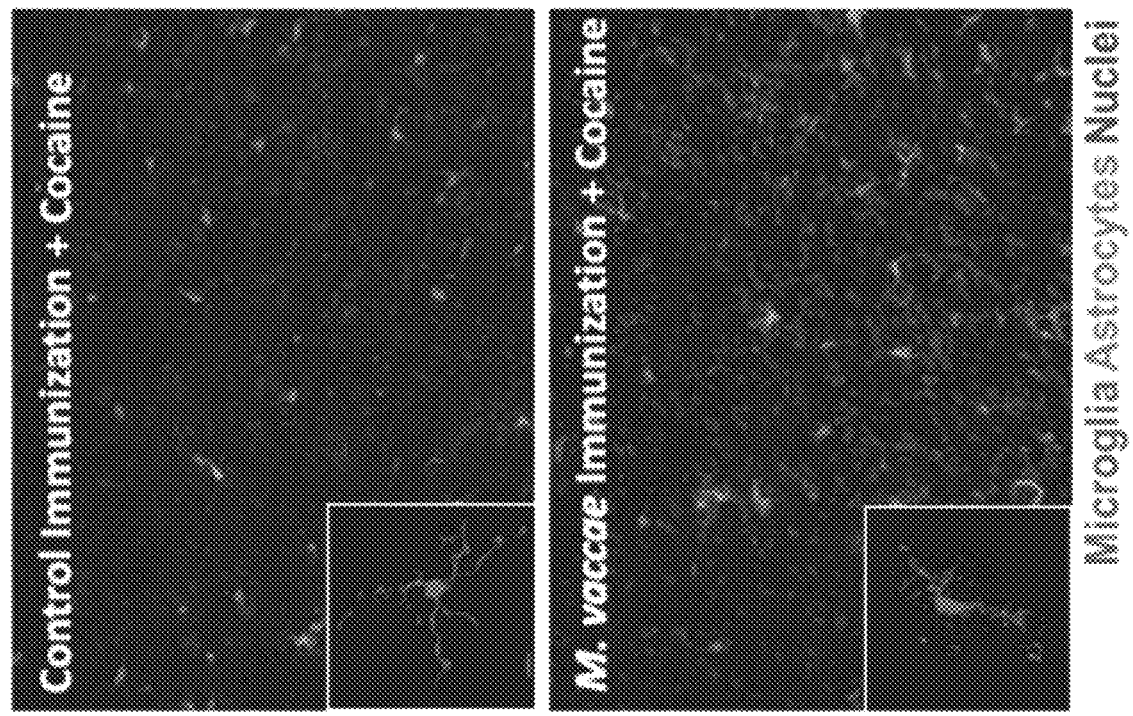

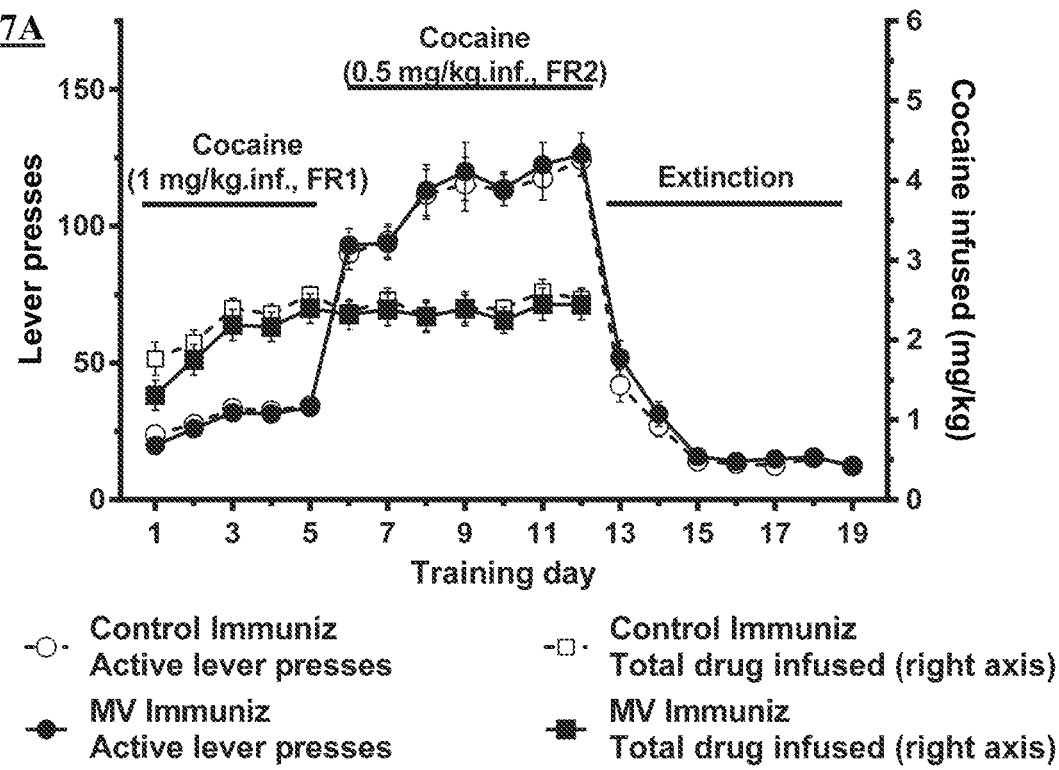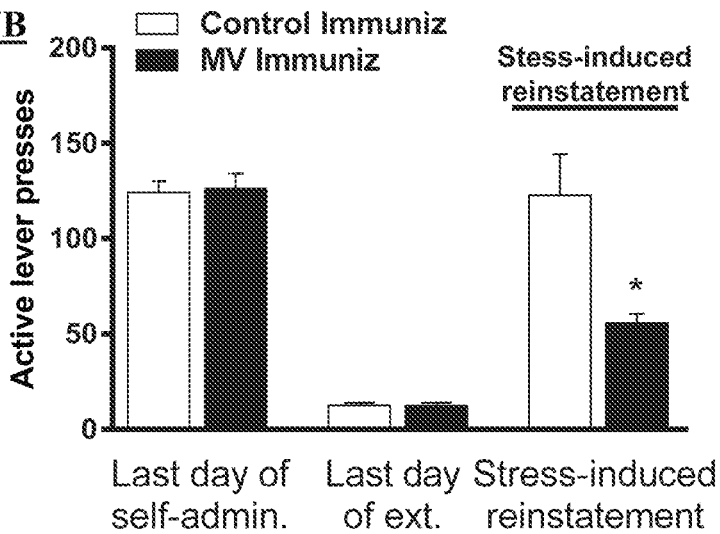

FIG. 8A Whole Brain Cytokines: P6
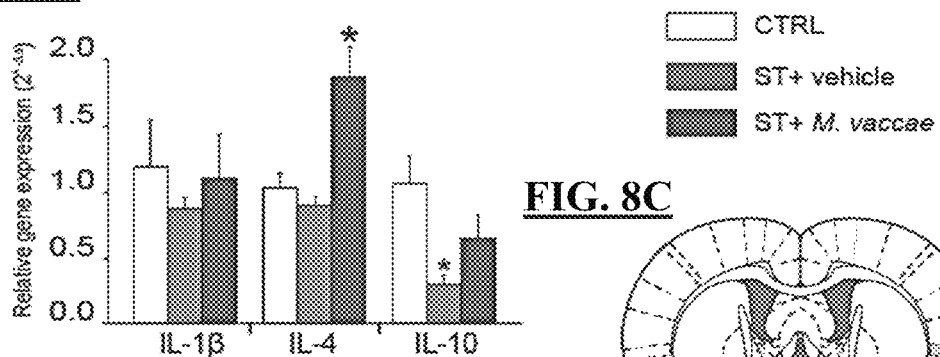
FIG. 8B Insular Cortex
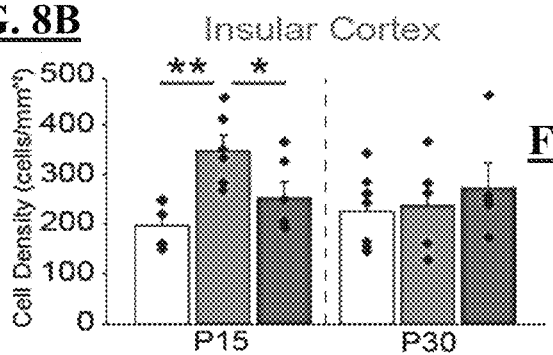
FIG. 8C
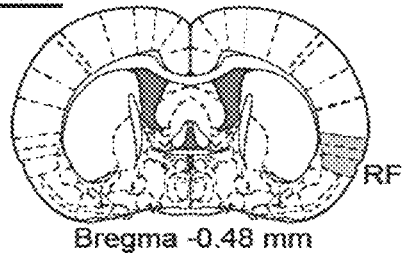
FIG. 8D
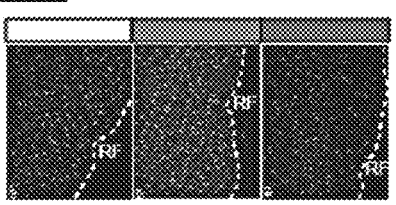
FIG. 8E Parietal Cortex
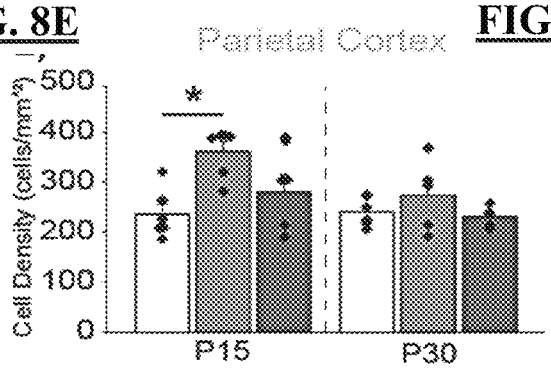
FIG. 8G
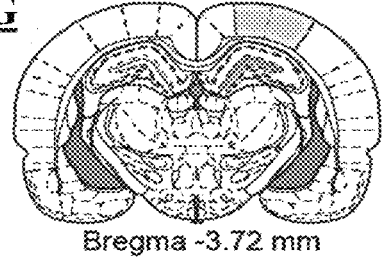
FIG. 8H
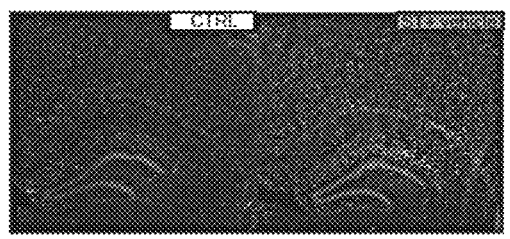
FIG. 8F Dentate Gyrus: Molecular Layer
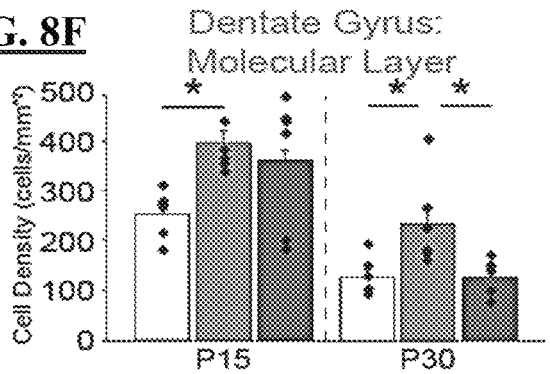
1.5 column

COMPOSITIONS AND METHODS FOR TREATING OR AMELIORATING COCAINE ADDICTION

CROSS-REFERENCE TO RELATED APPLICATIONS

This application claims priority to U.S. Provisional Patent Application Ser. No. 62/812,100 entitled "COMPOSITIONS AND METHODS FOR TREATING OR AMELIORATING COCAINE ADDICTION," filed Feb. 28, 2019, the disclosure of which is incorporated herein by reference in its entirety.

STATEMENT REGARDING FEDERALLY SPONSORED RESEARCH OR DEVELOPMENT

This invention was made with government support under DA041560-01A1 awarded by National Institutes of Health. The government has certain rights in the invention.

BACKGROUND OF THE INVENTION

Psychostimulant addiction is a major public health burden with no current FDA-approved treatment and a pressing need for new medications. Psychostimulants enhance dopamine signaling in the nucleus accumbens, resulting in euphoric effects that drive the drug-taking and drug-seeking behaviors leading to addiction. Chronic cocaine exposure also induces neuroinflammation, which may contribute to the pathophysiology underlying addiction and relapse.

There is thus a need in the art for identifying agents and compositions that can be used to treat, ameliorate, and/or prevent addiction to cocaine. The present disclosure addresses this need.

BRIEF SUMMARY OF THE INVENTION

The present invention provides in part a method of reducing, minimizing, or ameliorating a subject's desire to consume cocaine. In certain embodiments, the method comprises administering to the subject an effective amount of isolated *Mycobacterium*.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

FIG. 1A: Shock-elicited freezing across 2-min blocks after 2 shocks in a shuttle box, 24 h after exposure to inescapable shock (IS) or home cage control conditions. FIG. 1B: Shuttle box escape latencies for two FR1 trials and five blocks of five FR2 trials in the same rats tested in FIG. 1A. FIGS. 1C-1E: Effects of *M. vaccae* preimmunization on (FIG. 1C) baseline acoustic startle, a measure of generalized anxiety, (FIG. 1D) between-session extinction of fear-potentiated startle, and (FIG. 1E) within-session extinction of fear-potentiated startle. Fear conditioning in FIGS. 1C-1E occurred over two days, followed by extinction training starting 24 h later. FIG. 1F: *M. vaccae* preimmunization prevents stress-induced priming of hippocampal microglia, reflected by suppression of LPS-induced IL-1β release from microglia rapidly isolated from rats exposed to tailshock stress 24 hr prior and stimulated with LPS ex vivo. All data are from adult male rats and presented as means±SEM. *p<0.05, vs. vehicle-immunized controls; +p<0.05, vs. home cage controls; ## p<0.01, ### p<0.001 vs. vehicle-immunized controls.

FIG. 3 illustrates the finding that *M. vaccae* preimmunization altered morphological changes in microglia in the nucleus accumbens induced by repeated doses of 30 mg/kg cocaine. In a pilot experiment (n=4/group), male C57/Bl6 mice were preimmunized with heat-killed *M. vaccae* (3×0.1 mg, s.c.) or borate-buffered saline control prior to 7 consecutive days of cocaine (30 mg/kg, i.p.) or saline. Brains were removed 1 hr after the last cocaine exposure and sectioned. Anti-Iba1 antibodies, anti-GFAP antibodies, and DAPI were used to stain microglia, astrocytes, and nuclei, respectively. Images were processed and quantified in ImageJ by blinded observers. Microglial processes appeared more ramified in *M. vaccae*-immunized animals (insets); process lengths were analyzed in Imaris software. All data are means±SEM. N.D.=not yet determined.

FIGS. 7A-7B show certain simulated effects of *M. vaccae* pretreatment. FIG. 7A illustrates the finding that *M. vaccae* pretreatment did not significantly attenuate development of cocaine self-administration in male and female rats on a varied fixed-ratio (FR) schedule. Animals were immunized with heat-killed *M. vaccae* (3×0.1 mg, s.c.) or borate-buffered saline control prior to self-administration training. Following an initial 5 days of training on an FR1 schedule (1 mg/kg/infusion), and then 7 days of training on an FR2 schedule (0.5 mg/kg/infusion), all animals underwent extinction training in which lever presses resulted in no drug infusion. FIG. 7B shows that after 7 consecutive days of extinction training, all animals underwent stress-induced reinstatement testing. *M. vaccae* pretreatment significantly attenuated stress-induced cocaine-seeking behavior, as measured by active lever presses. All data are means±SEM.

FIGS. 8A-8H show that *M. vaccae* treatment induces an anti-inflammatory immunophenotype in the brain and mitigates region-specific developmental alterations in microglial number in ST animals. FIG. 8A shows mRNA expression levels of whole brain cytokines at P6, expressed as a ratio of control. FIGS. 8B, 8E, and 8F show cell density measures, expressed in terms of ionized calcium-binding adapter molecule 1-(Iba-1-) positive cells/mm$^2$, for each region of interest at P15 and P30. FIGS. 8C, 8G are illustrations of brain regions that were sampled for measurement of Iba1 immunostaining with the rhinal fissure (RF) for reference (pink, insular cortex; yellow, parietal cortex; green, dentate gyrus molecular layer). Equivalent adult rostrocaudal location, expressed in millimeters from bregma, is listed below each image. FIG. 8D shows representative images at 100× of Iba-1-positive cells in the insular cortex at P15 with the RF for reference for each group. FIG. 8H shows representative images at 40× of Iba-1-positive staining within the hippocampus and cortex, co-stained with DAPI for subregion localization at P15 in control and ST+vehicle animals. Bars represent means of each group, error bars represent +SEM, individual data points are plotted as diamonds. Results expressed as mean±SEM. *$P<0.05$, $P<0.01$, *$P<0.001$. Abbreviations: CTRL, control; IL, interleukin; *M. vaccae*, *Mycobacterium vaccae* NCTC 11659; P15, postnatal day 15; P30, postnatal day 30; RF, rhinal fissure; SEM, standard error of the mean; ST, stress-terbutaline.

(FIG. 9A) duration of submissive upright posture in s; (FIG. 9B) duration of avoiding behavior in s; (FIG. 9C) duration of scouting behavior in s; (FIGS. 9A-9C) data represent means+standard errors of the means. (FIG. 9D) shows the relationship between duration of submissive upright posture (s) and the duration of avoiding and scouting (s); circles indicate individual data points. *$p<0.05$, $p<0.01$, *$p<0.001$, post hoc pairwise comparisons between the groups indicated. Abbreviations: CDR, chronic disruption of rhythms; Mv, *Mycobacterium vaccae* NCTC 11659; NLD, normal light:dark cycle; SEM, standard errors of the means; Veh, borate-buffered saline vehicle.

DETAILED DESCRIPTION OF THE INVENTION

Figure 1A:
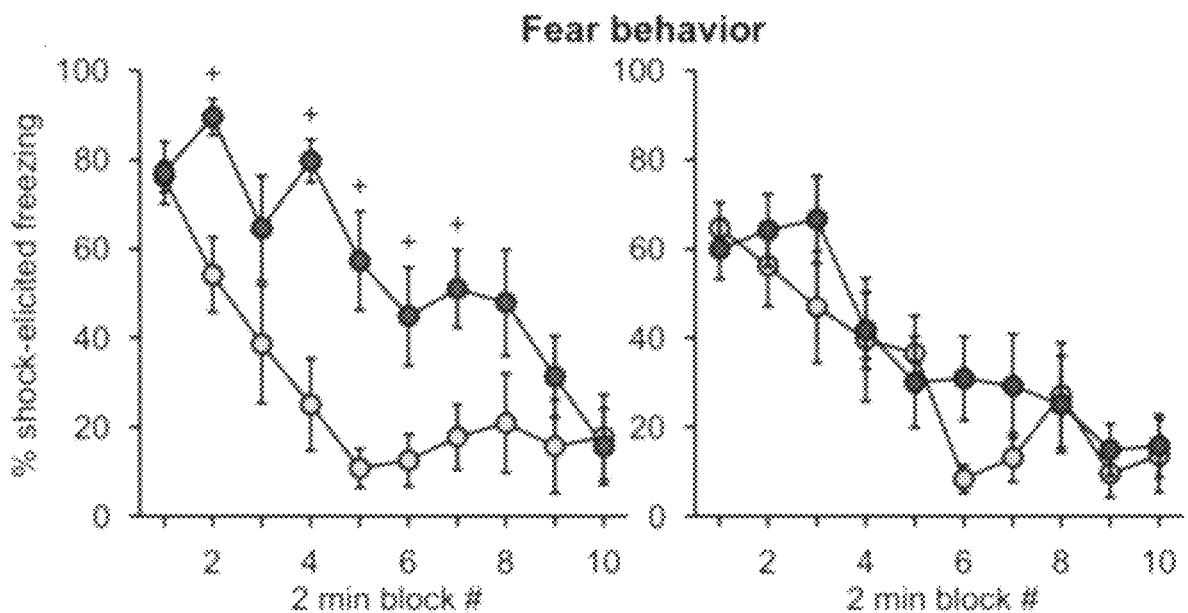
FIGS. 1A-1F illustrate the finding that immunization with *M. vaccae* (3×0.1 mg, s.c.) prevents stress-induced fear extinction resistance and enhances extinction of conditioned fear.

The present invention relates in part to the discovery of an immunization strategy as an anti-addiction and anti-relapse intervention, which could provide a unique treatment option for patients in addiction recovery.

Cocaine addiction and relapse are major public health concerns, but lack current FDA-approved pharmacological treatments. Thus, there is a pressing need to develop new therapies to treat cocaine addiction. The present disclosure relates in part to the evaluation of the translational potential of a novel immunotherapy—immunization with a heat-killed preparation of *M. vaccae*, a nonpathogenic environmental bacterium—for effects on the rewarding properties of cocaine and its potential to reduce relapse-like behavior.

Microbial signals are crucial in immunoregulation, which is indicated by a balanced expansion of regulatory T cells (Treg) and effector T cell populations. Exposure to nonpathogenic environmental bacteria, such as *Mycobacterium vaccae*, can reduce inappropriate inflammation in the periphery as well as stress-induced neuroinflammation. Specifically, immunization with heat-killed *M. vaccae* reduces inflammatory responses in murine models of stress-induced or chemically-induced colitis, reduces stress-induced anxiety, and enhances fear extinction in the fear-potentiated startle model. Furthermore, immunization with *M. vaccae* induces an anti-inflammatory cytokine milieu in the brain and prevents stress-induced sensitization of hippocampal microglia. Importantly, *M. vaccae* immunization dramatically alters serotonin signaling in the brain, reducing stress- and anxiety-like responding in animal models of post-traumatic stress disorder and other anxiety disorders. Stress can accelerate the development of drug addiction and is a major trigger for relapse. In certain embodiments, the immunoregulatory, anti-stress, and anxiolytic effects of *M. vaccae* immunization reduces addiction- and relapse-like responding in models of cocaine addiction and alter the development of cocaine-induced neuroinflammation.

Effects of *M. vaccae* immunization on behavioral responses in tests of cocaine conditioned place preference (CPP) and stress-induced reinstatement of cocaine CPP were tested. *M. vaccae* immunization did not alter acquisition of CPP to 30 mg/kg cocaine but abolished stress-induced reinstatement of cocaine CPP. These data provide the first assessment of the translational potential of *M. vaccae* immunotherapy to treat substance use disorders. Given the excellent safety record of *M. vaccae* immunotherapy in clinical trials, successfully demonstrating an anti-relapse effect in preclinical models justifies rapid clinical evaluation of treatment efficacy.

DISCLOSURE

In certain embodiments, the invention contemplates the use of an isolated *Mycobacterium* for treating, ameliorating, and/or preventing cocaine addiction in a subject. In certain embodiments, the isolated *Mycobacterium* is administered to the subject before or immediately after a patient has desire to consume cocaine.

In certain embodiments, the isolated *Mycobacterium* is administered one time, or more than one time, to the subject. In other embodiments, the isolated *Mycobacterium* is administered before, or around the time, the subject has desire to consume cocaine and continues to be administered to the patient thereafter. In yet other embodiments, the isolated *Mycobacterium* is administered to the subject after the subject has desire to consume cocaine.

In certain embodiments, the isolated *Mycobacterium* comprises heat-killed *Mycobacterium*. In certain embodiments, mycobacterial species for use in the present invention include *M. vaccae*, *M. thermoresistibile*, *M. flavescens*, *M. duvalii*, *M. phlei*, *M. obuense*, *M. parafortuitum*, *M. sphagni*, *M. aichiense*, *M. rhodesiae*, *M. neoaurum*, *M. chubuense*, *M. tokaiense*, *M. komossense*, *M. aurum*, *M. indicus pranii*, *M. tuberculosis*, *M. microti*, *M. africanum*,

*M. kansasii, M. marinum, M. simiae, M. gastri, M. nonchromogenicum, M. terrae, M. triviale, M. gordonae, M. scrofulaceum, M. paraffinicum, M. intracellulare, M. avium, M. xenopi, M. ulcerans, M. diernhoferi, M. smegmatis, M. thamnopheos, M. flavescens, M. fortuitum, M. peregrinum, M. chelonei, M. paratuberculosis, M. leprae, M. lepraemurium*, and any combinations thereof.

In certain embodiments, the heat-killed *Mycobacterium* is non-pathogenic. In certain embodiments, the non-pathogenic heat-killed *Mycobacterium* is chosen from *M. vaccae, M. obuense, M. parafortuitum, M. aurum, M. indicus pranii, M. phlei*, and any combinations thereof. In certain embodiments, the non-pathogenic heat-killed *Mycobacterium* is a rough variant. The amount of isolated *Mycobacterium* administered to the subject is sufficient to elicit a protective immune response in the patient such that it eliminates or minimizes the subject's desire to consume cocaine.

In certain embodiments, the subject is administered an effective amount of heat-killed *Mycobacterium*, which typically may be from $10^3$ to $10^{11}$ organisms, in a non-limiting example from $10^4$ to $10^{10}$ organisms, in a non-limiting example from $10^6$ to $10^{10}$ organisms in a non-limiting example from $10^6$ to $10^9$ organisms per unit dose. The effective amount of heat-killed *Mycobacterium* for use in the present invention can be from $10^3$ to $10^{11}$ organisms, in a non-limiting example from $10^4$ to $10^{10}$ organisms, in a non-limiting example from $10^6$ to $10^{10}$ organisms, in a non-limiting example from $10^6$ to $10^9$ organisms. In certain embodiments, the amount of heat-killed *Mycobacterium* for use in the present invention is from $10^7$ to $10^9$ cells or organisms. In a non-limiting example, the composition according to the present invention is administered at a dose of from $10^8$ to $10^9$ cells for human and animal use. In a non-limiting example, the composition according to the present invention is administered at a dose from 0.01 mg to 1 mg or 0.1 mg to 1 mg organisms presented as either a suspension or dry preparation.

In certain embodiments, effective amounts of *Mycobacterium* are administered in multiple (repeat) doses, for example two or more, three or more, four or more, five or more, ten or more, or twenty or more repeat doses, at intervals of about 2 weeks, or about 4 weeks or about 8 weeks.

In certain embodiments, the isolated *Mycobacterium* is administered to the subject using the parenteral, oral, sublingual, nasal or pulmonary route. In certain embodiments, the isolated *Mycobacterium* is administered using a parenteral route selected from subcutaneous, intradermal, subdermal, intraperitoneal, intravenous, and intravesicular injection. In certain embodiments, administration by the parenteral route does not comprise injection of mycobacterial cell wall extract. Intradermal injection enables delivery of an entire proportion of the mycobacterial composition to a layer of the dermis that is accessible to immune surveillance and thus capable of electing appropriate immune response at local lymph nodes.

In certain embodiments, the isolated *Mycobacterium* is administered orally, including by suspension, tablets and the like. In certain embodiments, liquid formulations are administered by inhalation of lyophilized or aerosolized microcapsules. In certain embodiments, additional pharmaceutical vehicles are used to control the duration of action of the preparation. They can be entrapped in microcapsules prepared by coacervation techniques or by interfacial polymerization (hydroxymethylcellulose or gelatin microcapsules) in colloidal drug delivery systems (for example, liposomes, albumin microspheres, micro-emulsions, nanoparticles and nanocapsules) or in macro-emulsions. Excipients, for example, salts, various bulking agents, additional buffering agents, chelating agents, antioxidants, cosolvents, and the like can be included in the final formulation.

In certain embodiments, initial administration of the isolated *Mycobacterium* is followed by further doses of the isolated *Mycobacterium* 2 weeks later and continuing every 2 weeks for the next 3 doses followed by 4 weeks without treatment. Patients may receive the isolated *Mycobacterium* every 4 weeks for up to 12 months or longer following the first dose given. Alternatively, dosing may involve weekly administration following the priming or initial dose.

In certain embodiments, the effective amount of the isolated *Mycobacterium* is administered as a single dose. In certain embodiments, the effective amount of the isolated *Mycobacterium* is administered in multiple (repeat) doses, for example two or more, three or more, four or more, five or more, ten or more, or twenty or more repeat doses. In certain embodiments, the isolated *Mycobacterium* is administered between about 4 weeks and 1 day prior to an anticipated traumatic event, more preferably between about 4 weeks and 1 week, or about between 3 weeks and 1 week, or about between 3 weeks and 2 weeks. Administration may be presented in single or multiple doses.

A container according to the invention in certain instances may be a vial, an ampoule, a syringe, capsule, tablet or a tube. In certain embodiments, the isolated *Mycobacterium* is lyophilized and formulated for resuspension prior to administration. In certain embodiments, the mycobacteria are suspended in a volume of a pharmaceutically acceptable liquid. In certain embodiments, the invention provides a container comprising a single unit dose of mycobacteria suspended in pharmaceutically acceptable carrier wherein the unit dose comprises about $1 \times 10^6$ to about $1 \times 10^{10}$ mycobacteria. In certain embodiments, the liquid comprising suspended mycobacteria is provided in a volume of between about 0.1 ml and 10 ml, or about 0.5 ml and 2 ml. In certain embodiments, the composition comprising mycobacteria in a containment means is frozen (i.e., maintained at less than about 0° C.).

In certain embodiments, attenuated *Mycobacterium* is administered to specific sites on or in a subject. For example, the mycobacterial compositions according to the invention may be administered adjacent to lymph nodes. Thus, in certain instances, sites of administration of a mycobacterial composition are near the posterior cervical, tonsillar, axillary, inguinal, anterior cervical, sub-mandibular, sub mental or superclavicular lymph nodes. Such sites of administration may be on the right side, on the left side, or on both sides of the body. In certain embodiments, mycobacterial compositions are delivered close to the axillary, cervical, and/or inguinal lymph nodes. For example, a dosage of the mycobacteria may distribute into tissues adjacent to the right and left axillary lymph node and the right and left inguinal lymph nodes.

In certain embodiments, a dosage of mycobacteria is administered to a subject by intradermal injection wherein the dosage is distributed to the axillary and inguinal on both sides of the body and wherein there are two injections (i.e., two wheals) at each site.

In certain embodiments, methods of the invention involve the administration of 2, 3, 4, 5, 6, 7, 8, 9, 10 or more doses of mycobacteria separated by a period of one day or more. In certain embodiments, such separate doses are separated by several days, one week, two weeks, one month, or more. In certain embodiments, methods according to the invention may comprise administering 1 to 5 doses of mycobacteria over a period of three weeks or more. In certain embodiments, methods of the invention comprise administering 1 to 5, 1 to 4, 1 to 3, 1 to 2 or 2 doses of mycobacteria over a period of about three weeks. Each dose administered may be the same or different dosage relative to a previous or subsequent dose administration. In certain embodiments, it is preferred that a dosage of mycobacteria is lower than any dosage that was previously administered. In certain embodiments, a dose of mycobacteria is administered at about half of the dosage that was administered in any previous treatment.

Mycobacterial compositions according to the invention will comprise an effective amount of mycobacteria typically dispersed in a pharmaceutically acceptable carrier. The preparation of an pharmaceutical composition that contains mycobacteria will be known to those of skill in the art in light of the present disclosure, as exemplified by Remington's Pharmaceutical Sciences, 18th Ed. Mack Printing Company, 1990, Moreover, for animal (e.g., human) administration, it will be understood that parenteral preparations should meet sterility, pyrogenicity, general safety and purity standards. A specific example of a pharmacologically acceptable carrier is borate buffer or sterile saline solution (0.9% NaCl).

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In one embodiment, the compositions of the invention are formulated using one or more pharmaceutically acceptable excipients or carriers. In one embodiment, the pharmaceutical compositions of the invention comprise a therapeutically effective amount of an agent of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

In one embodiment, the present invention is directed to a packaged pharmaceutical composition comprising a container holding a therapeutically effective amount of an agent of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of an agent of the present invention depends on the age, sex and weight of the patient, the current medical condition of the patient and the progression of a disease or disorder contemplated in the invention. The skilled artisan is able to determine appropriate dosages depending on these and other factors.

A suitable dose of an agent of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Combination Therapies

In certain embodiments, the compounds of the invention are useful in the methods of the invention in combination with at least one additional agent useful for treating or preventing the diseases or disorders contemplated herein. This additional agent may comprise compounds identified herein or compounds, e.g., commercially available compounds, known to treat, prevent or reduce the symptoms of the diseases or disorders contemplated herein in a subject.

A synergistic effect may be calculated, for example, using suitable methods such as, for example, the Sigmoid-Emax equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Kits

The invention includes a kit comprising at least one composition contemplated in the invention, an applicator, and an instructional material for use thereof. The instructional material included in the kit comprises instructions for preventing, ameliorating, or treating cocaine addiction in a subject. The instructional material recites the amount of, and frequency with which, the agent should be administered to the subject. In other embodiments, the kit further comprises at least one additional agent for preventing, ameliorating, or treating cocaine addiction in a subject.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, each of the following terms has the meaning associated with it in this section.

Generally, the nomenclature used herein and the laboratory procedures in cell culture, molecular genetics, pharmacology, and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity or frequency of at least one sign or symptom of the disease or disorder experienced by a patient is reduced.

As used herein, the terms "analog," "analogue," or "derivative" are meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically.

By the term "applicator," as the term is used herein, is meant any device including, but not limited to, a hypodermic syringe, a pipette, and the like, for administering the compounds and compositions of the invention.

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Isolated" means altered or removed from the natural state. For example, a nucleic acid or a peptide naturally present in a living animal is not "isolated," but the same nucleic acid or peptide partially or completely separated from the co-existing materials of its natural state is "isolated." An isolated nucleic acid or protein may exist in substantially purified form, or may exist in a non-native environment such as, for example, a host cell.

As used herein, the term "modulate" is meant to refer to any change in biological state, i.e. increasing, decreasing, and the like. For example, the term "modulate" may be construed to refer to the ability to regulate positively or negatively the expression, stability or activity of a target protein, including but not limited to transcription of a target protein mRNA, stability of a target protein mRNA, translation of a target protein mRNA, target protein stability, target protein post-translational modifications, target protein activity, or any combination thereof. Further, the term modulate may be used to refer to an increase, decrease, masking, altering, overriding or restoring of activity, including but not limited to, target protein activity.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

"Parenteral" administration of a composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary, intracranial and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

As used herein, a "subject" refers to a human or non-human mammal. Non-human mammals include, for example, livestock and pets, such as ovine, bovine, porcine, canine, feline and murine mammals. In certain embodiments, the subject is human.

A "therapeutic" treatment is a treatment administered to a subject who exhibits signs of pathology, for the purpose of diminishing or eliminating those signs.

As used herein, the term "therapeutically effective amount" is an amount of a compound of the invention, that when administered to a patient, ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his or her own knowledge and to this disclosure.

As used herein, "treating a disease or disorder" means reducing the frequency with which a symptom of the disease or disorder is experienced by a patient. Disease and disorder are used interchangeably herein.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms. As used herein, the term "wild-type" refers to the genotype and phenotype that is characteristic of most of the members of a species occurring naturally and contrasting with the genotype and phenotype of a mutant.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Methods and Materials

Example 1

Immunoregulation, the balanced expression of regulatory T cells (Treg) and effector T cells (Th1, Th2, and Th17), is under control of microbial signals. Environmental microbial exposures, including to the ubiquitous nonpathogenic soil bacterium *M. vaccae*, may contribute key signals that modulate immune activity. The hygiene hypothesis, in which reduced exposure to microbial signals (due to lifestyle factors and increased hygiene) is hypothesized to lead to inadequate immunoregulation and chronic, low-grade inflammation, has driven research into treatments for allergic and autoimmune disorders that expose patients to these missing microbial signals. Immunization with heat-killed *M. vaccae* produces long-term (2-5 weeks following immunization) immunoregulatory effects, reducing inflammatory responses in murine models of stress-induced colitis and stress-induced exaggeration of chemically induced colitis (Reber, et al., 2016, Proc. Natl. Acad. Sci. U.S.A. 113: E3130-3139). Clinical trials confirmed immunoregulatory effects in patients with tuberculosis: *M. vaccae* immunotherapy recipients had a significantly faster return toward normal tumor necrosis factor (TNF) serum values than placebo recipients (Dlugovitzky, et al., 2006, Respir. Med. 100:1079-1087). The protective effects of *M. vaccae* in murine models of asthma, and the stress-protective effects, are dependent on induction of Treg and production of anti-inflammatory cytokines, including IL-10 and transforming growth factor (TGF)-β (Reber, et al., 2016, Proc. Natl. Acad. Sci. U.S.A. 113:E3130-3139). These are expected to be persistent effects due to the long half-life of Treg cells—newly differentiated Treg have a half-life of 27 days in mice—which may contribute to the long-lasting stress-protective effects of *M. vaccae*.

The long-term goal of the proposed research is to develop new interventions to treat pyschostimulant addiction. In certain embodiments, the immunoregulatory, anti-stress, and anxiolytic effects of *M. vaccae* immunization reduce addiction- and relapse-like responding in rat models of cocaine addiction and reduce cocaine-induced neuroinflammation. The effects of *M. vaccae* immunization on behavioral responses in tests of response-contingent cocaine self-administration as well as cue- and stress-induced reinstatement of cocaine-seeking behavior, a model of relapse, are tested. Further, it is evaluated how *M. vaccae* immunization alters the neuroinflammatory response to cocaine exposure via immunohistochemistry.

Figure 1B:
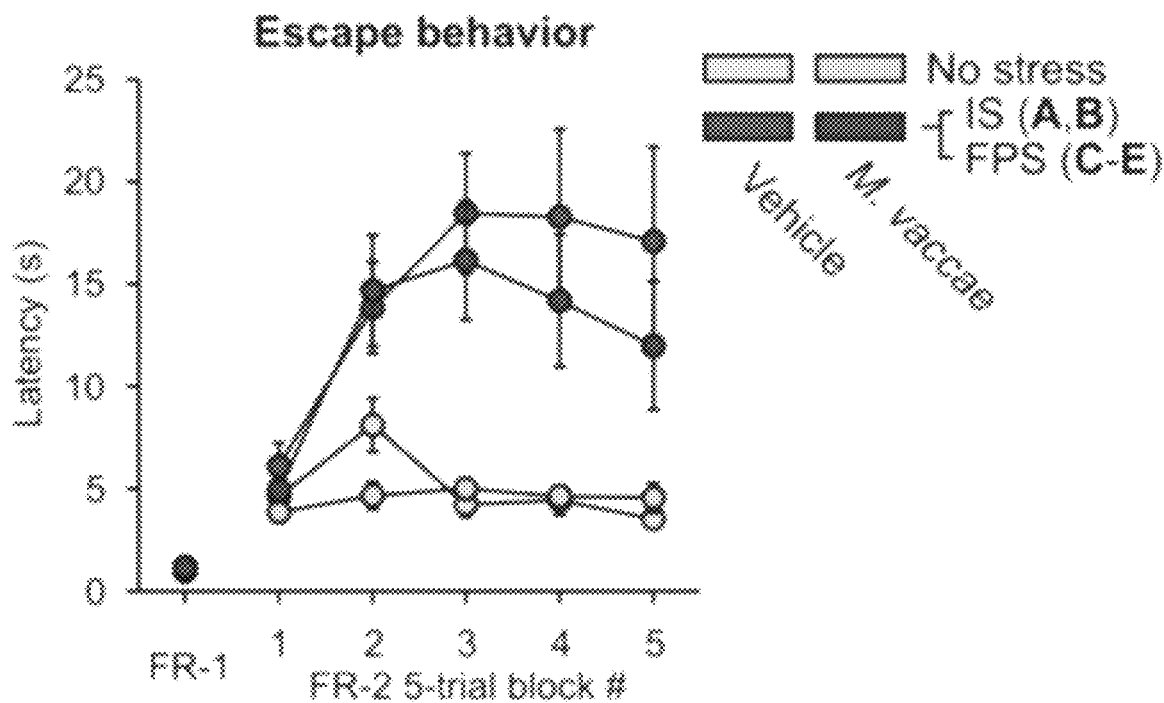
Figure 1C:
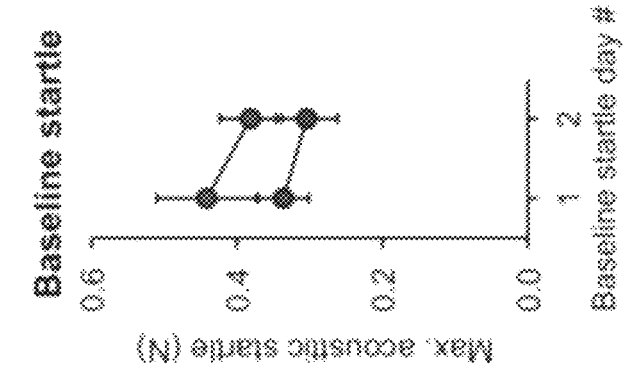
Figure 1D:
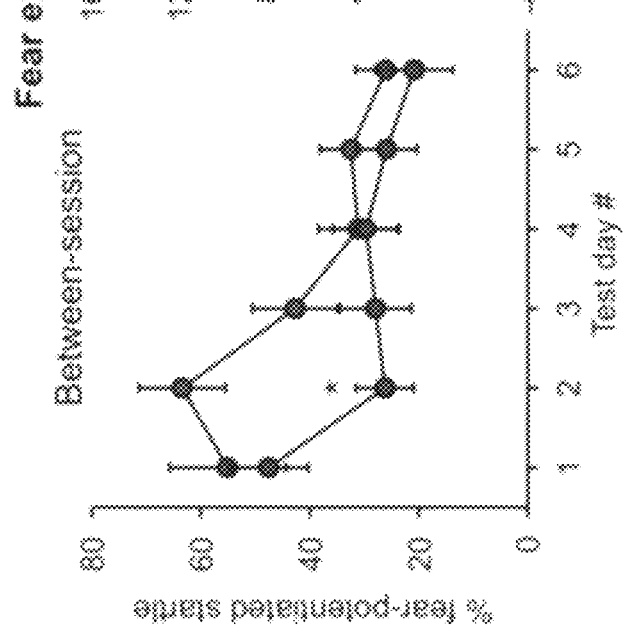
Figure 1E:
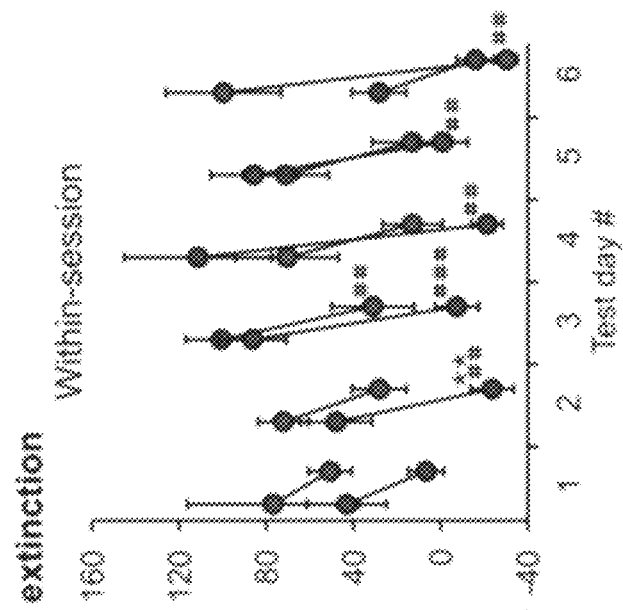
Figure 1F:
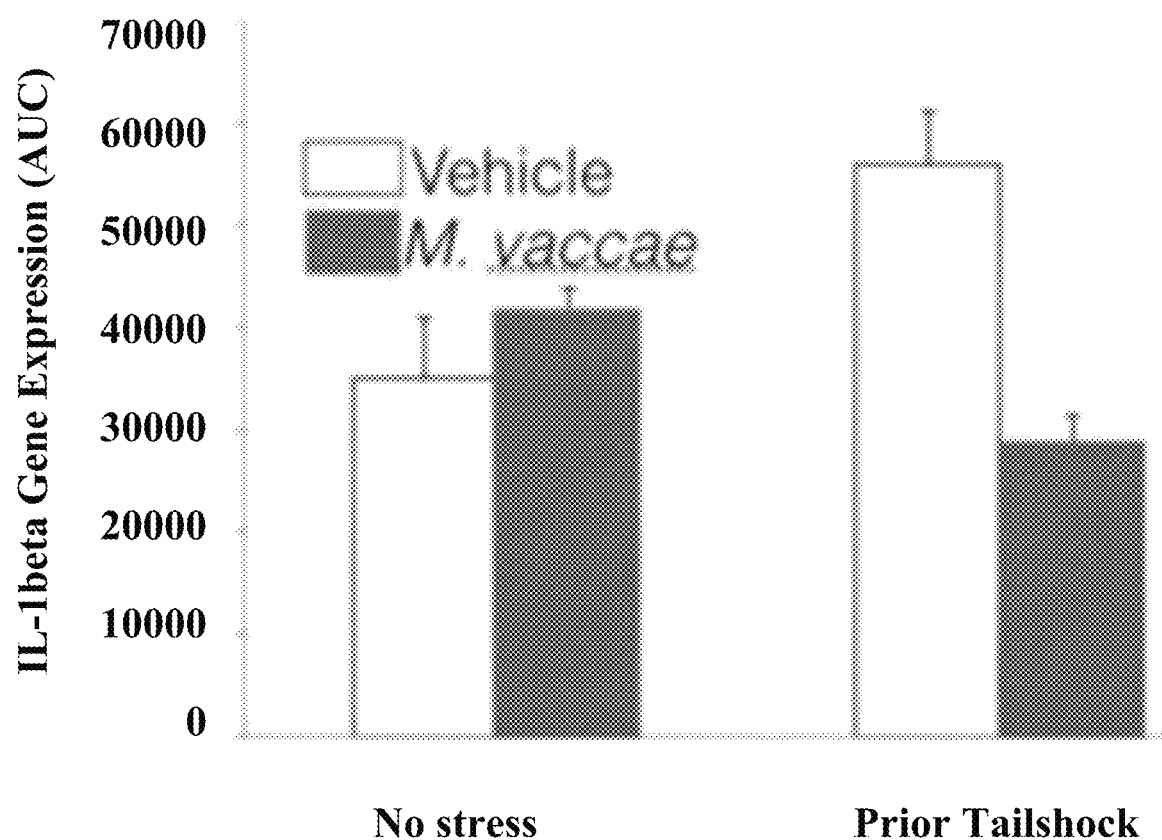

Example 2: *M. vaccae* Preimmunization Reduces Anxiety-Like Behavior and Responses to Stress Immunization with a heat-killed preparation of *M. vaccae* (NCTC 11659; 0.1 mg, s.c., in 100 μL of borate-buffered saline vehicle) reduces stress responses and anxiety-like behavior in a variety of rodent animal models. In addition to the stress resilience effects of *M. vaccae* immunization in mice, immunization with *M. vaccae* in rats reduces fear expression in a model of learned helplessness (FIGS. 1A-1B), and enhances within-session and between-session fear extinction in the fear-potentiated startle model (FIGS. 1C-1E). These effects were associated with *M. vaccae*-induced alterations of htr1a and tph2 mRNA expression, encoding the 5-HT1A receptor and tryptophan hydroxylase 2 (the rate-limiting enzyme in the biosynthesis of serotonin), respectively, in the dorsal raphe nucleus. Three once-weekly doses of heat-killed *M. vaccae* set up a long-enduring whole-body anti-inflammatory state, reflected by establishment of a Treg-dominant immune profile, and shifting of brain microglia to a stable anti-inflammatory state (FIG. 1F), indicated by attenuated release of IL-1β from adult hippocampal microglia stimulated with lipopolysaccharide (LPS) ex vivo 24 h following tailshock stress. *M. vaccae* immunization after fear conditioning (on days 1, 8, and 15 following fear conditioning) enhances fear extinction tested starting on day 36. Immunization with *M. vaccae* in rats has anxiolytic effects in the elevated T-maze, without affecting escape behaviors, indicating that *M. vaccae* immunization reduces inhibitory avoidance, without affecting escape or panic-like behaviors.

Example 3: *M. vaccae* Preimmunization Reduces Stress-Induced Reinstatement of Cocaine CPP The underlying principle of CPP is that, when paired with primary reinforcers (e.g., cocaine), contextual/environmental stimuli acquire secondary rewarding properties via Pavlovian/classical conditioning. Exposure to stressful stimuli can both increase vulnerability to the rewarding effects of cocaine, and also serve to reinstate previously-extinguished cocaine CPP. Indeed, stress and anxiety are risk factors for addiction disorders. Cocaine is well-characterized in rodent CPP models, and stress factors alter cocaine-induced CPP. CPP can be extended into a model of relapse-like behavior using an extinction-reinstatement paradigm in which reinstatement of the drug place preference can be induced by stress or drug priming as a model of relapse-like behavior that corresponds reliably to drug self-administration and reinstatement of drug-seeking behaviors following self-administration procedures.

Figure 2:
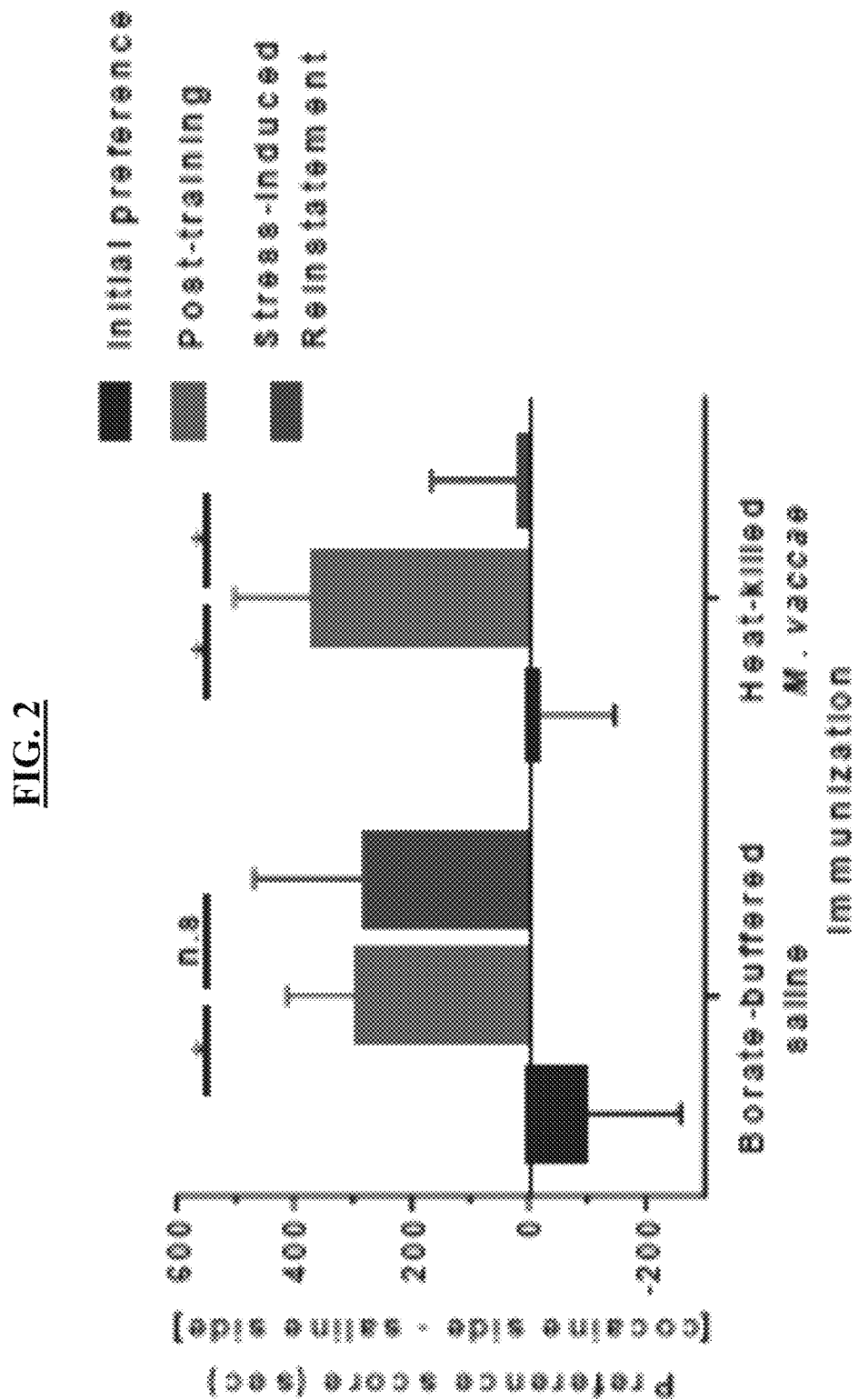
FIG. 2 illustrates the finding that *M. vaccae* immunization did not alter acquisition of CPP to 30 mg/kg cocaine but abolished stress-induced reinstatement of cocaine CPP. Animals were preimmunized with heat-killed *M. vaccae* (3×0.1 mg, s.c.) or saline control prior to 10 days of cocaine CPP training using an unbiased procedure, both groups showed a significant preference for the cocaine-paired side (green). After two extinction sessions, reinstatement was induced by forced swim test (blue). All data are means±SEM. *p<0.05, 2-way RM-ANOVA with Sidak's multiple comparisons test.
Figure 4:
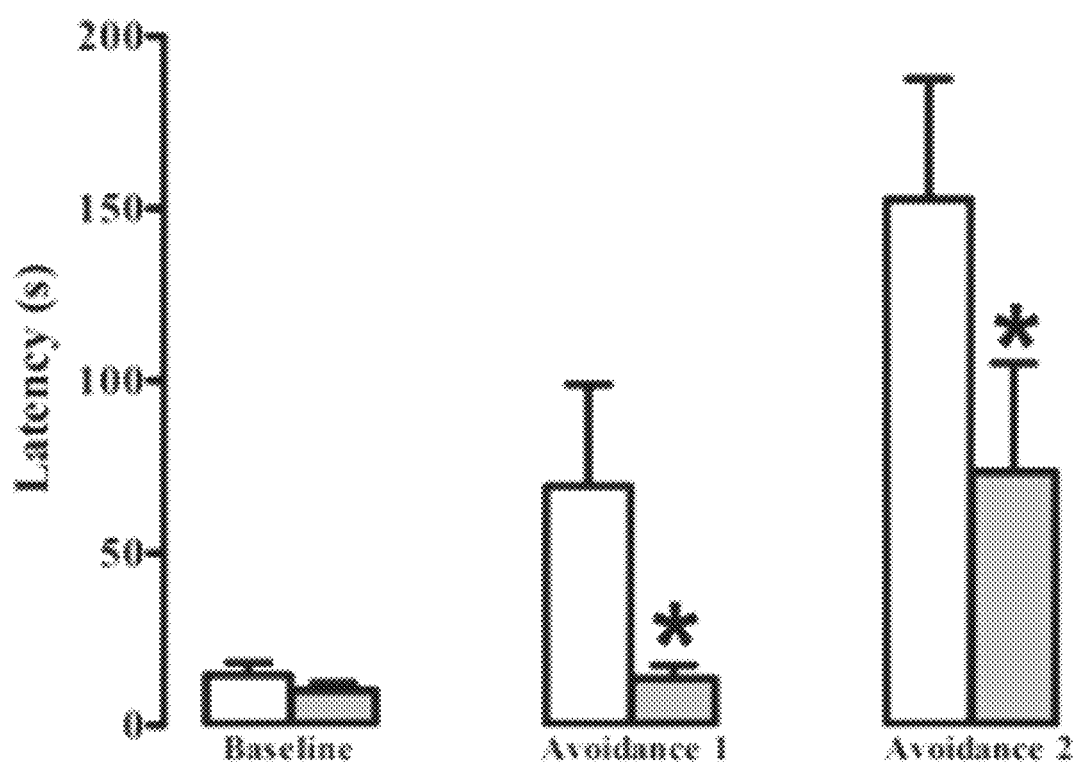
FIG. 4 illustrates the finding that *M. vaccae* immunization has anxiolytic effects in the elevated T-maze in male rats. Animals were immunized with heat-killed *M. vaccae* (3×0.1 mg, s.c.) or borate-buffered saline control prior to testing in elevated T-maze. *M. vaccae*-treated animals (gray) had reduced inhibitory avoidance latencies compared to saline controls (white) measured in the elevated T-maze. All data are mean±SEM * p<0.05.
Figure 5:
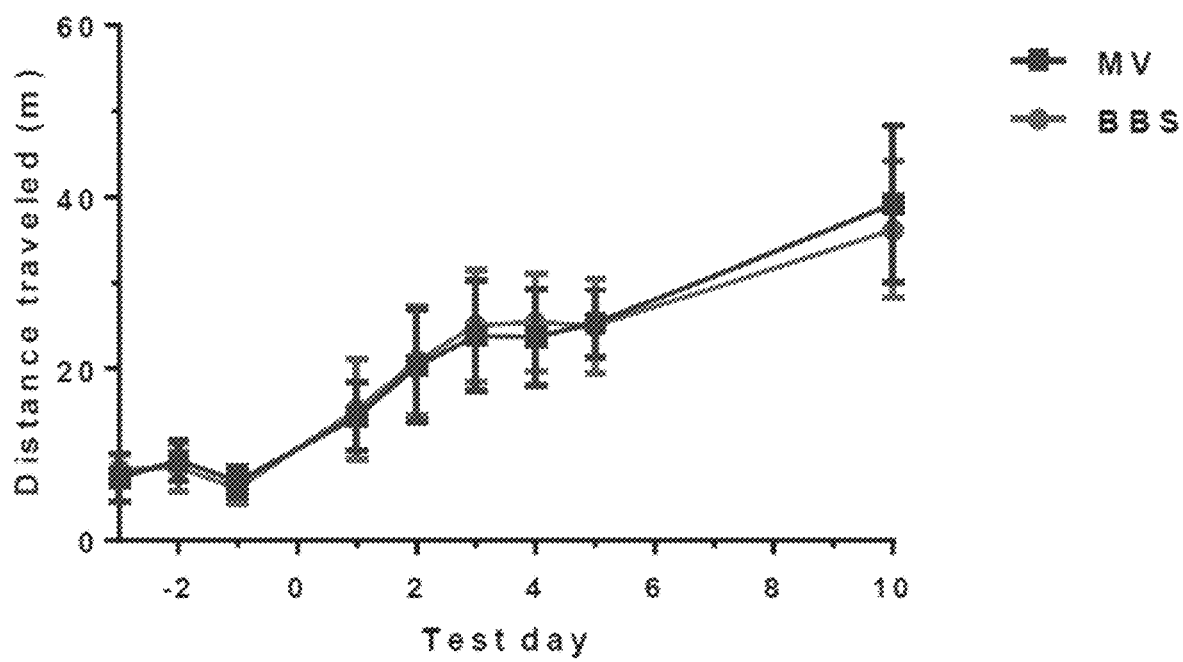
FIG. 5 illustrates the finding that *M. vaccae* pretreatment did not significantly attenuate locomotor sensitization induced by repeated doses of 10 mg/kg cocaine in male mice. Animals were immunized with heat-killed *M. vaccae* (3×0.1 mg, s.c.) or borate-buffered saline control prior to cocaine sensitization. Following 3 days of baseline open-field familiarization, both groups were given 5 consecutive days of cocaine (10 mg/kg, i.p.) and locomotor activity was analyzed for 40 minutes following cocaine injection. Five days following the last cocaine dose, a challenge dose of 10 mg/kg cocaine was administered and locomotor activity was analyzed for 40 minutes. All data are means±SEM.
Figure 6:
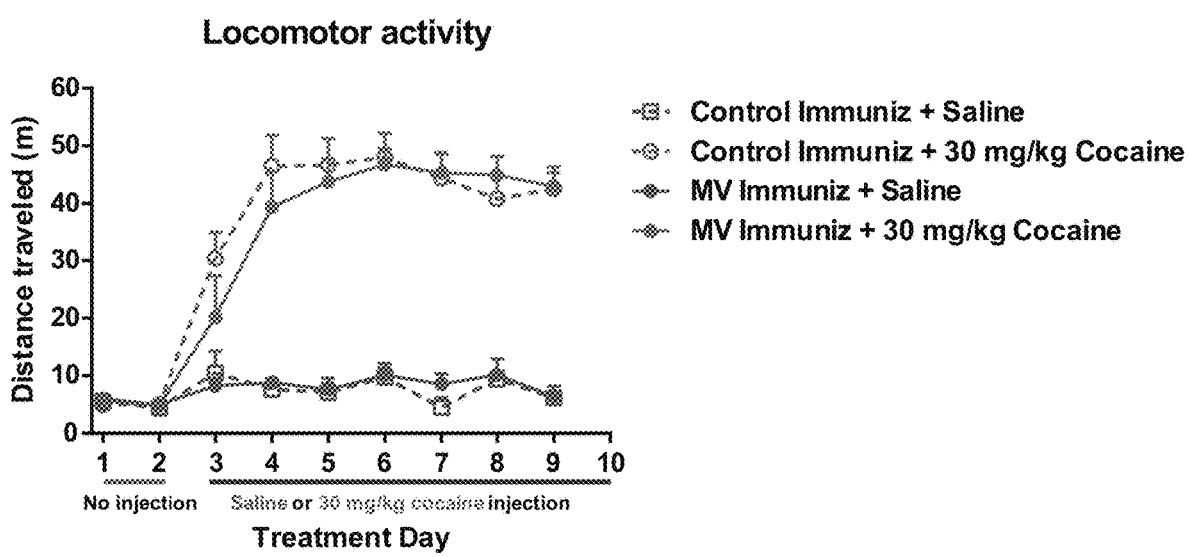
FIG. 6 illustrates the finding that *M. vaccae* pretreatment did not significantly attenuate locomotor activity induced by repeated doses of 30 mg/kg cocaine, not significantly affect locomotor activity in response to saline injections, in male mice. Animals were immunized with heat-killed *M. vaccae* (3×0.1 mg, s.c.) or borate-buffered saline control prior to cocaine sensitization. Following 2 days of baseline open-field familiarization, both groups were given 7 consecutive days of cocaine (30 mg/kg, i.p.) and locomotor activity was analyzed for 40 minutes following cocaine injection. All data are means±SEM.

In a study using male C57BL/6 mice, *M. vaccae* preimmunization did not alter acquisition or expression of CPP to 30 mg/kg cocaine, but significantly attenuated stress-induced reinstatement of cocaine CPP induced by a forced swim stressor (FIG. 2).

Example 4

The experiments use adult male and female Long-Evans rats, an outbred strain well-characterized in addiction models. There are important differences in behavioral and physiological responses to drugs of abuse in rodents and humans; thus it is necessary to test both males and females. The *M. vaccae* immunization protocol used for the studies uses injections of heat-killed *M. vaccae* (0.1 mg, s.c.) or vehicle (borate-buffered saline) once per week for three consecutive weeks. This 3×0.1 mg, s.c., regimen has been determined to provide reliable, robust immune responses correlated with significant neurological and behavioral responses in mice and rats.

In certain embodiments, *M. vaccae* preimmunization attenuates cocaine self-administration and reinstatement, and alters the development of cocaine-induced neuroinflammation. The experiments test whether *M. vaccae* preimmunization can disrupt the reinforcing effects of cocaine by testing for shifts in the cocaine dose-response curves in self-administration, as well as drug-seeking following exposure to stressors or cocaine-associated cues in reinstatement paradigms. In certain embodiments, *M. vaccae* preimmunization shifts the cocaine dose-response curve or attenuates cocaine-induced neuroinflammation, and this indicates a protective effect against the abuse-related effects of cocaine.

Example 5

This study helps determine whether *M. vaccae* preimmunization alters cocaine-taking and cocaine-seeking behaviors in cocaine self-administration and reinstatement models.

In order to determine whether *M. vaccae* preimmunization can alter cocaine-taking or cocaine-seeking behaviors, preimmunized rats are trained to self-administer cocaine. They are then tested in either a multiple-dose procedure or a progressive ratio procedure to evaluate effects on the rewarding properties of self-administered cocaine. *M. vaccae* preimmunization is tested for effects in cue- and stress-induced reinstatement of cocaine-seeking behaviors, a model of relapse.

This sub-study helps detect immunization-dependent effects on the reinforcing effects of cocaine. In certain embodiments, *M. vaccae*-mediated rightward or downward shifts in cocaine dose-response relationships or reductions in reinstatement induced by drug cues or stress provide evidence that *M. vaccae* preimmunization is protective against development of cocaine addiction or help prevent relapse to cocaine addiction.

General Cocaine Self-Administration Method.

Experimentally naïve Long-Evans rats are initially trained in operant testing chambers to lever press in order to earn a palatable food reward. Following successful operant training, rats are prepared for i.v. cocaine self-administration by surgical catheterization of the right external jugular vein using standard aseptic surgical techniques. During experimental sessions, catheters are connected to an injection pump that deliver set volumes of cocaine dissolved in saline at predetermined doses described elsewhere herein. Catheter patency is maintained via daily flushes with heparinized saline solution.

After recovery from surgery, each rat is allowed to lever press for i.v. cocaine (0.5 mg/kg/infusion) on a fixed ratio 2 (FR2) reinforcement schedule. This dose of cocaine lies within the descending limb of the cocaine self-administration dose-response curve, in which reliable self-administration is maintained. Cocaine infusions are associated with presentation of a stimulus light and tone. To avoid cocaine overdose, rats are limited to no more than 60 cocaine injections per 2-hour session. Studies using rat cocaine self-administration procedures similar to those described below typically use n=10-12 per treatment condition. Power analysis with standard α and β parameters (0.05 and 0.80, respectively) using estimated means and variance from these studies, suggests that n=10 per treatment condition appropriately power these proposed studies. To account for potential loss of catheter patency, an additional two animals are allocated for each group tested.

Determine Effects of *M. vaccae* Preimmunization on the Rewarding Value of Cocaine Using Self-Administration.

These studies in one non-limiting aspect help determine whether *M. vaccae* preimmunization alters the subjective rewarding properties of cocaine as assessed by alterations in the patterns of cocaine-taking behavior in two response-contingent cocaine self-administration paradigms: progressive ratio (PR) responding and a single-session multiple-dose (SSMD) paradigm. Rats preimmunized with *M. vaccae* (3×0.1 mg, s.c.) or vehicle control are trained to stably self-administer 0.5 mg/kg/infusion cocaine on an FR2 schedule as described elsewhere herein and then are assigned to either PR or SSMD groups.

PR self-administration follows a schedule in which each successive cocaine infusion requires increased lever press responding according to a progression based on the formula response ratio=$[5e^{inj\,number \times 0.2}]-5$;

Each session continues until the breakpoint (BP) is reached, defined as the maximal completed lever press workload resulting in a cocaine infusion before a 1-hr period during which no infusion was earned. Three unit doses (0.25, 0.5, and 1.0 mg/kg/infusion; counterbalanced dose order presentation) are tested in the PR schedule. Rats receive standard FR2 re-training (0.5 mg/kg/infusion) for 3 days between PR test sessions.

SSMD self-administration follows a schedule in which cocaine self-administration is maintained on an FR2 schedule by a full range of cocaine doses (0, 0.125, 0.25, 0.5, 1.0 mg/kg/infusion) presented in successive trials within a single session. Cocaine doses are presented in ascending order across five 20-min trials, with 20-min time-out periods between trials. The dose-response curve is considered stable after 3 consecutive sessions where the number of infusions earned at each available cocaine dose varies <10%.

Determine Effects of *M. vaccae* Immunization on Stress- or Cue-Induced Reinstatement of Cocaine-Seeking Behavior.

These studies in one non-limiting aspect help determine whether *M. vaccae* preimmunization attenuates cocaine-seeking behavior as assessed by the stress- and cue-induced reinstatement reinstatement model of relapse, and thus whether the immunization has potential anti-relapse effects. Rats preimmunized with *M. vaccae* (3×0.1 mg, s.c.) or vehicle control are trained to stably self-administer 0.5 mg/kg/infusion cocaine on an FR2 schedule as described elsewhere herein, and then are assigned to either cue- or stress-induced rein-statement groups. Animals destined for cue-induced reinstatement undergo extinction training, wherein lever presses have no scheduled consequences, until responding on the previously-reinforced active lever is reduced to <20% of self-administration responding. For cue-induced reinstatement tests, the cocaine-associated light & tone are presented 5 times immediately prior to the session, and are then presented with each completed FR2 thereafter. Animals destined for stress-induced reinstatement undergo extinction training in which each completed FR2 results in presentation of the cocaine-associated cues, but no drug delivery, until extinction criteria (see elsewhere herein) are met. Stress-induced reinstatement is induced by 15 minutes of intermittent footshock presented within the operant chamber, immediately prior to the reinstatement test (Kupferschmidt, et al., 2011, J. Vis. Exp. 2265).

In certain embodiments, *M. vaccae* immunization reduces the rewarding effects of cocaine as measured by rightward/downward shifts in the PR and SSMD cocaine dose-response curves. In certain embodiments, *M. vaccae* immunization attenuates cue- and stress-induced reinstatement of cocaine-seeking behavior. In certain embodiments, the anti-inflammatory/anti-stress effects of *M. vaccae* immunization can reduce drug-taking and drug-seeking behaviors, supporting the translational potential of *M. vaccae* immunization as a treatment for cocaine addiction and relapse.

Example 6

This study helps determine how *M. vaccae* preimmunization alters cocaine-induced neuroinflammation and microglial activation.

In order to determine how *M. vaccae* preimmunization affects the development of cocaine-induced neuroinflammatory responses, neurochemical and immunohistochemical analyses are performed on nucleus accumbens and hippocampal tissue taken from preimmunized rats trained to self-administer cocaine or given non-contingent i.p. injections of cocaine. Microglial morphology and cytokine profiles are analyzed in treatment and control tissues.

This sub-study helps determine how *M. vaccae* immunotherapy affects the neuroinflammatory responses to prolonged cocaine exposure, potentially identifying mechanisms to exploit in further drug development.

Cocaine induces neuroinflammation in a variety of brain regions, with variable effects based on exposure patterns and evaluated markers. In certain embodiments, the present study helps confirm that *M. vaccae* preimmunization induces an anti-inflammatory milieu in the hippocampus, ventral tegmental area (VTA), and nucleus accumbens (NAc), and determine whether immunization alters cocaine-induced neuroinflammation and microglial activation.

General Detection of Neuroinflammation.

*M. vaccae* immunization and/or cocaine exposure can alter several markers; the experiments detailed elsewhere herein use separate populations of rats to identify patterns of neuroinflammatory responses. Fresh frozen brain tissue from the hippocampus, VTA, and NAc is used to detect changes in cytokine levels and neuroinflammatory mediators (IL-4, IL-1β, Tnf, IL-6, Nf-kbia, Nlrp3 and Hmgb1) via ELISA and Western blot, and RT-PCR is used to detect changes in mRNA expression levels of IL-4 and IL-4-responsive genes Cd200r1, Cd206 (Mrc1), and Nos2 (Frank, et al, 2018, Brain Behav. Immun. 73:352-363). For some techniques, one hemisphere is used for protein analyses and the other for genetic analyses. For others, sample pooling may be necessary, particularly for the smaller VTA and NAc regions.

Microglial morphology is assessed via Iba1, Nos2, and Arginase staining in fixed brain tissue, which can reveal whether microglia have been activated in response to cellular damage. Nos2 is released as a pro-inflammatory response, and induction of Nos2 happens in response to cocaine. Nos2 is decreased in microglia after exposure to IL-4, and increased levels of arginase are observed in activated microglia when exposed to IL-4. In certain embodiments, cocaine increases Nos2 staining in microglia, while *M. vaccae* immunization decreases Nos2 and increases Arginase staining, in certain non-limiting embodiments by increasing the anti-inflammatory cytokine IL-4. Astrocyte reactivity is assessed by GFAP staining, which can reveal the presence of oxidative stress. Cellular types are quantified and correlated with cocaine exposure and immunization status. Morphological changes in microglia can indicate a reactive state and are investigated using high-magnified (63×) confocal images and the Imaris software "Filament Tracer" tool, to analyze the number of branches, junctions, and the average and maximum length of branches in microglia. In certain non-limiting embodiments, 12 animals/treatment condition provide sufficient material for the planned analyses.

Determine Effects of *M. vaccae* Preimmunization on an Anti-Inflammatory Milieu and Cocaine-Induced Inflammation in Non-Contingent Models.

These studies in one aspect help determine whether preimmunized with *M. vaccae* (3×0.1 mg, s.c.) or vehicle control have altered neuroinflammation in response to acute or chronic cocaine delivered by i.p. injections. In an acute exposure experiment, rats are given a single injection of saline or 30 mg/kg cocaine, i.p. In a chronic exposure experiment, rats are given saline or 30 mg/kg cocaine, i.p., for seven days. Cocaine exposures start 24 h after the final immunization with *M. vaccae* or vehicle. Rat brains are taken 2 h after the final injection of cocaine or vehicle. This is a 2 (vehicle vs. *M. vaccae*)×3 (control vs. acute cocaine vs. chronic cocaine) factorial design.

Determine Effects of *M. vaccae* Preimmunization on Cocaine-Induced Inflammation in Self-Administration Models.

In order to understand how *M. vaccae* preimmunization may be altering behavioral patterns, neuroinflammatory markers are assessed in animals that self-administer cocaine. Rats preimmunized with *M. vaccae* (3×0.1 mg, s.c.) or vehicle control are trained to stably self-administer 0.5 mg/kg/infusion cocaine at an FR2 schedule or are used as yoked saline controls. Following 14 days of cocaine self-administration, rat brains are taken 2 h after the final injection of cocaine or vehicle. This is a 2 (vehicle vs. *M. vaccae*)×2 (cocaine self-administering vs. yoked saline) factorial design.

In certain embodiments, *M. vaccae* immunization induces an anti-inflammatory milieu in the hippocampus, VTA, and NAc (i.e., increased expression of IL-4 mRNA and IL-4-responsive genes, such as Cd200r1, Cd206 (Mrc1), and Nos2), and attenuates induction of proinflammatory cytokines following cocaine administration. In certain embodiments, immunization with *M. vaccae* reduces the production of Nos2 and increases the expression of Arginase in activated microglia which can effectively deactivate NOS2 and reduce nitric oxide (NO) generation. Without wishing to be limited by any theory, the behavioral changes observed in immunized mice after cocaine exposure can be linked to a decrease of NO in microglia.

FIG. 3 illustrates the finding that repeated cocaine administration (30 mg/kg cocaine, i.p., for seven straight days; tissue samples acquired 1 hr after last cocaine injection) can induce a neuroinflammatory response as indicated by the increase in IBA1+ cell area within the NAc, but that *M. vaccae* preimmunization produced distinct morphological differences in microglial cells (more ramified), resulting in enhanced IBA1+ area with no increase in cell numbers over cocaine-free controls. Classically, microglial reactivity is associated with morphological changes that include enlarged cell bodies, retracted processes and thicker processes. The results indicate that microglia are activated differently in the immunized state. More detailed investigation of morphological features, using high-resolution confocal imaging and Imaris software analysis, suggest that microglial process length and ramification differ substantially between *M. vaccae* and control immunized animals exposed to cocaine.

Example 7

ST rats express increased hippocampal gliosis compared to controls, suggesting a prolonged neuroinflammatory trajectory in this model that could be altered by *M. vaccae* and explain its effect on attenuating ASD-like behavior. Whole-brain levels of several cytokines were therefore measured. To separate possible anti-inflammatory effects of *M. vaccae* immunization in dams from subsequent treatment of the pups, we measured cytokines at P6, after the final terbutaline injection, but prior to the first offspring injection of *M. vaccae* to see if this stress-protective anti-inflammatory phenotype was present during postnatal ST. Significant group differences existed in whole brain mRNA levels of IL-4 ($F_{(2,9)}$=12.6, P<0.01) and IL-10 ($F_{(2,9)}$=5.6, P<0.05) at this time point. As shown in FIG. 8A, P6 pups from vehicle-treated ST dams demonstrated significantly lower levels of IL-10 compared to control (P<0.05), while P6 pups from *M. vaccae*-treated ST dams displayed significantly higher levels of IL-4 than both controls (P<0.05) and P6 pups from vehicle-treated ST dams (P<0.01). This anti-inflammatory phenotype existed prior to the first offspring injection with *M. vaccae*, suggesting that the maternal neuroinflammatory protection conferred by *M. vaccae* is incorporated into offspring through a maternal transfer mechanism.

Microglia are the principle innate immune cells of the CNS, not only responsible for release of both pro- and anti-inflammatory cytokines, but also instrumental for early developmental processes such as synaptogenesis. Thus, neuroinflammatory protection conferred by *M. vaccae* could be reflected in changes in microglial function. Changes in CNS microglial density at two critical periods of neurodevelopment were examined; at P15 (when microglial density is at a developmental peak and actively guiding synapse development) and at P30, where many neurodevelopmental processes should be close to reaching adult levels.

At P15, significant between-group differences in microglial density were observed in the insular cortex (FIGS. 8B, 8D; $F_{(2,15)}$=8.2, P<0.01), parietal cortex (FIG. 8E; $F_{(2,14)}$=6.9, P<0.01), and the molecular layer of the dentate gyrus (FIGS. 8F, 8H; $F_{(2,15)}$=4.1, P<0.05). No differences were observed in other brain regions, including the dentate hilus ($F_{(2,14)}$=0.6, P=0.581) and primary somatosensory cortex ($F_{(2,14)}$=0.7, P=0.518) (data not shown). Post hoc analysis demonstrated that ST+vehicle rats had higher cell density counts than controls in insular cortex (FIG. 8B; n=6; 354.0±25.3 cells/mm²; P<0.01), parietal cortex (FIG. 8E; n=6; 350.3±19.1 cells/mm²; P<0.01), and in the dentate molecular layer (FIGS. 8F, 8H; n=6; 401.6±25.4 cells/mm²; P<0.01). In the insula, microglia density in ST+*M. vaccae* rats was reduced (258.5±30.6 cells/mm²; P<0.05) compared to ST+vehicle rats and could not be distinguished from control animals (201.0±19.9 cells/mm²; P=0.142) (FIG. 8B). However, microglia density in ST+*M. vaccae* rats was variable in both the parietal cortex (FIG. 8E; n=5; 271.9±34.5 cells/mm²) and the dentate molecular layer (FIG. 8F; n=6; 366.3±55.5 cells/mm²) and did not significantly differ from controls or ST+vehicle rats.

By P30, there were no significant group differences in microglial density in the insular or parietal cortices, or dentate hilus. However, significant group differences were still present in the molecular layer of the dentate gyrus (FIG. 8F; P30; $F_{(2,14)}$=5.7, P<0.05), with ST+vehicle rats maintaining elevated levels (n=6; 238.5±37.7 cells/mm²) when compared to controls (n=6; 129.9±15.8 cells/mm²; P<0.05). In contrast to P15 in the dentate gyrus, ST+*M. vaccae* animals also had reduced density counts (n=5; 129.2±17.4 cells/mm²) when compared to ST+vehicle rats (P<0.05).

Observed microglia remained highly ramified, and we found no qualitative morphological evidence of amoeboid microglia. However, ANOVA revealed group differences in cell size, only within the insular cortex, at P15 ($F_{(2,15)}$=3.89, P<0.05). Post hoc analysis demonstrated that ST+vehicle rats had larger detected size on average (n=6; 124.9±11.0 μm²) compared to controls (n=6; 91.8±8.41 μm²) (P<0.05). However, cell size for ST+*M. vaccae* animals (n=6; 97.1±7.25 μm²) failed to reach significance when compared to control (P=0.64) or vehicle treated rats (P=0.06).

Example 8

Social Defeat

Figure 9B:
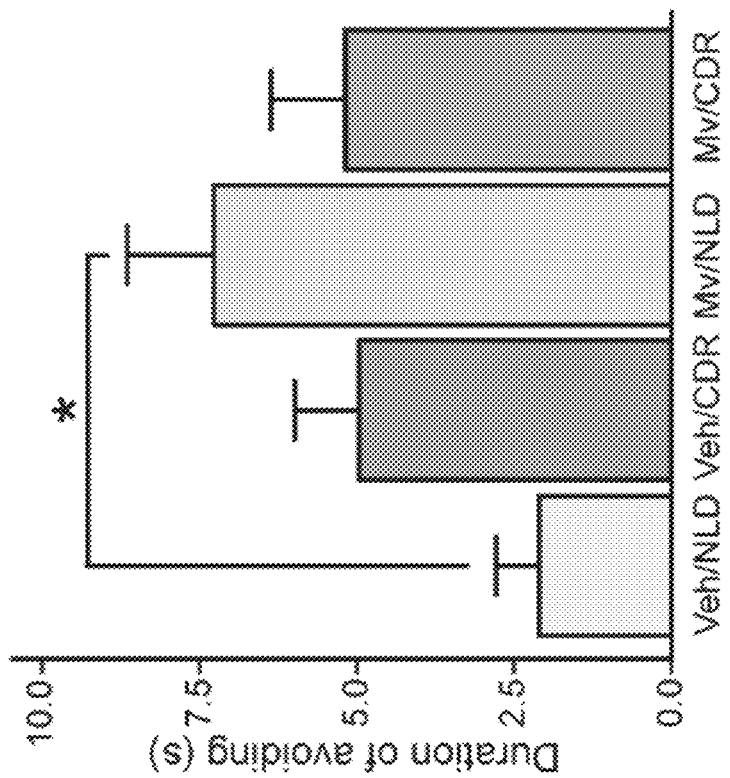
FIGS. 9A-9D show behavioral responses of experimental mice during the social defeat test. Individual panels represent.
Figure 9A:
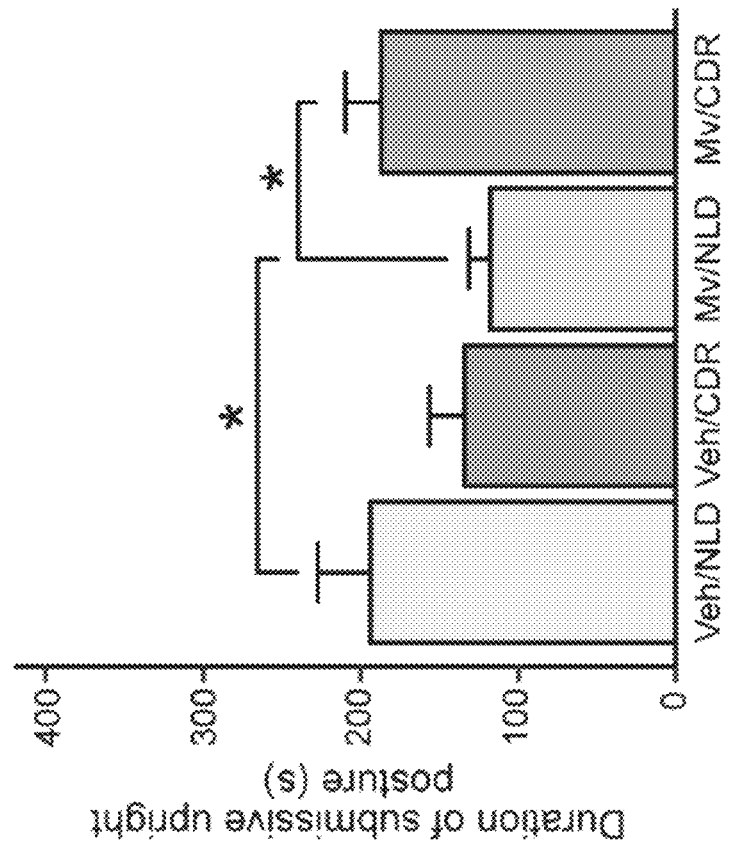
Figure 9D:
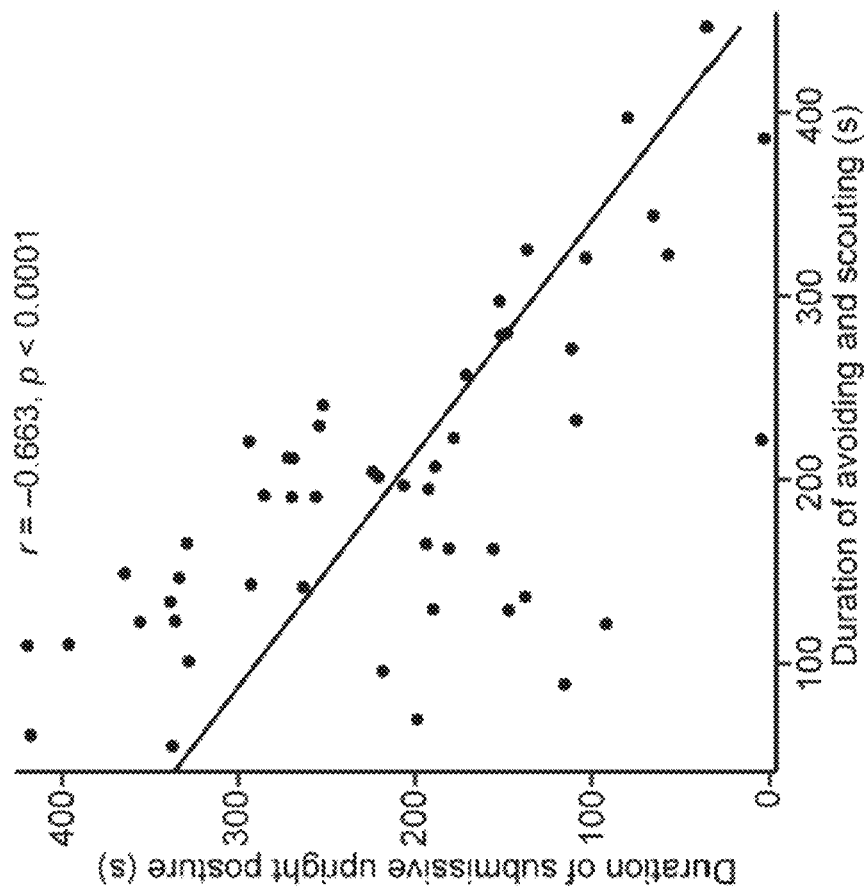
Figure 9C:
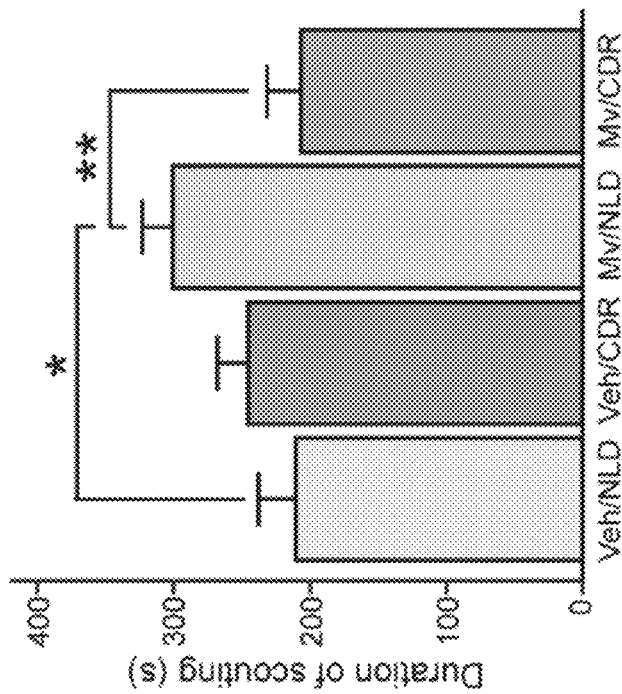

Analysis of the duration of submissive upright posture (in seconds) in the SD test using an overall LMM approach revealed an interaction effect of Mv treatment ch revet=2.58, p=0.013). Among NLD mice, immunization with Mv, relative to Veh-treated controls, decreased the duration of submissive upright posture (p=0.034; Table 1; FIG. 9A). Conversely, among Mv-15 immunized mice, CDR increased submissive upright posture relative to NLD control mice (p=0.044; Table 1; FIG. 9B). Similar analysis on the duration of avoiding revealed an interaction effect of Mv treatment analyst=eatmentp=0.047). Post hoc pairwise comparisons showed an increase in avoiding among Mv-treated NLD mice relative to Veh-treated controls (p=0.003; Table 1; FIG. 9B). Analysis of the duration of scouting demonstrated an interaction effect of Mv treatment f CDR (t=R (mentp=0.014) and a main effect of CDR (t=2.695, p=0.010). Post hoc pairwise comparisons showed an increase in duration of scouting among Mv-treated NLD mice relative to Veh-treated NLD mice (p=0.014; Table 1; FIG. 9C). Additionally, Mv-treated CDR mice 612 showed a decrease in duration of avoiding compared to Mv-treated NLD mice (p=0.008; Table 1; FIG. 9C). Duration of avoiding and scouting behaviors combined, two of the behaviors observed most frequently in the SD test, was inversely correlated to the duration of submissive upright posture (Pearson inr=right pp<0.0001; FIG. 9D).

TABLE 1

Group means ± standard errors of the means (SEM) of each measurable behavior in the social defeat test.

Part 1/2:

| Treatment group | Avoiding (s) | Scouting (s) | Flight (s) | Submissive upright posture |
|---|---|---|---|---|
| Veh/NLD | 1.75 ± 0.61 | 210.66 ± 27.12 | 17.47 + 3.14 | 193.82 ± 33.47 |
| Veh/CDR | 4.58 ± 1.01 | 245.18 ± 22.55 | 19.59 + 2.98 | 134.26 ± 21.93 |
| Mv/NLD | 7.27 ± 1.38** | 300.74 ± 21.95* | 21.54 + 3.75 | 117.65 ± 13.75* |
| Mv/CDR | 4.81 ± 1.15 | 206.87 ± 24.76§§ | 21.57 + 4.26 | 187.13 ± 22.77§ |

Part 2/2:

| Treatment group | Attacks received (s) | Mounts received (s) | Chase received (s) | Inactivity (s) | Total activity (s) |
|---|---|---|---|---|---|
| Veh/NLD | 14.90 ± 2.94 | 46.97 ± 8.70 | 1.22 ± 0.37 | 93.66 ± 27.63 | 580.44 ± 5.44 |
| Veh/CDR | 13.08 ± 1.88 | 62.06 ± 15.51 | 0.78 ± 0.25 | 70.18 ± 21.65 | 549.71 ± 26.31 |

TABLE 1-continued

Group means ± standard errors of the means (SEM)
of each measurable behavior in the social defeat test.

| | | | | | |
|---|---|---|---|---|---|
| Mv/NLD | 17.30 ± 2.62 | 82.41 ± 26.59 | 1.86 ± 0.80 | 37.42 ± 10.68 | 586.18 ± 4.42 |
| Mv/CDR | 13.40 ± 1.88 | 56.18 ± 14.65 | 1.04 ± 0.44 | 66.73 ± 12.52 | 557.73 ± 23.81 |

Pairwise comparisons indicated by
*p < 0.05 and
**p < 0.01, Veh/NLD against Mv/NLD group;
§p < 0.05 and
§§p < 0.01, Mv/NLD against Mv/CDR group.
Abbreviations:
CDR, chronic disruption of rhythms;
Mv, *Mycobacterium vaccae* NCTC 11659;
NLD, normal light:dark cycle;
Veh, borate-buffered saline vehicle

Enumerated Embodiments

The following exemplary embodiments are provided, the numbering of which is not to be construed as designating levels of importance:

Embodiment 1 provides a method of reducing, minimizing, or ameliorating a subject's desire to consume cocaine, the method comprising administering to the subject an effective amount of isolated *Mycobacterium.*

Embodiment 2 provides the method of Embodiment 1, wherein the subject's desire to consume cocaine is caused by at least one factor selected from the group consisting of fear, stress, and anxiety.

Embodiment 3 provides the method of any of Embodiments 1-2, wherein the isolated *Mycobacterium* comprises a whole cell *Mycobacterium.*

Embodiment 4 provides the method of any of Embodiments 1-3, wherein the isolated *Mycobacterium* comprises a non-pathogenic heat-killed *Mycobacterium.*

Embodiment 5 provides the method of Embodiment 4, wherein the non-pathogenic heat-killed *Mycobacterium* is selected from the group consisting of *M. vaccae, M. obuense, M. parafortuitum, M. aurum, M. indicus pranii,* and any combinations thereof.

Embodiment 6 provides the method of any of Embodiments 4-5, wherein the non-pathogenic heat-killed *Mycobacterium* is selected from the group consisting of *M. vaccae* and *M. obuense.*

Embodiment 7 provides the method of any of Embodiments 1-6, wherein the isolated *Mycobacterium* is a rough variant.

Embodiment 8 provides the method of any of Embodiments 1-7, wherein the isolated *Mycobacterium* is administered to the subject as a vaccine composition optionally comprising an adjuvant.

Embodiment 9 provides the method of any of Embodiments 1-8, wherein the isolated *Mycobacterium* is administered more than once to the subject.

Embodiment 10 provides the method of any of Embodiments 1-9, wherein the subject is administered from about $10^7$ to $10^9$ cells of nonpathogenic heat-killed *Mycobacterium.*

Embodiment 11 provides the method of any of Embodiments 1-10, wherein the subject is administered the *Mycobacterium* by a route selected from the group consisting of parenteral, oral, sublingual, nasal, and pulmonary.

Embodiment 12 provides the method of Embodiment 11, wherein the parenteral route is selected from the group consisting of subcutaneous, intradermal, subdermal, intraperitoneal, intravenous, and intravesicular injection.

Embodiment 13 provides the method of any of Embodiments 1-12, wherein the subject is addicted to cocaine.

Embodiment 14 provides the method of any of Embodiments 1-13, wherein the subject is a mammal.

Embodiment 15 provides the method of Embodiment 14, wherein the mammal is human.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing the likelihood of or preventing a human subject's relapse into cocaine consumption, wherein the human subject had previously self-administered cocaine, the method comprising:

- identifying a human subject currently exposed to at least one risk factor for relapse into cocaine self-administration;
- administering to the human subject an effective amount of isolated non-pathogenic heat-killed *Mycobacterium vaccae;*
- thereby reducing the likelihood of or preventing the human subject's relapse into cocaine self-administration.

2. The method of claim 1, wherein the at least one risk factor is selected from the group consisting of fear, stress, and anxiety.

3. The method of claim 1, wherein the isolated non-pathogenic heat-killed *Mycobacterium vaccae* is administered to the human subject as a vaccine composition.

4. The method of claim 1, wherein the isolated non-pathogenic heat-killed *Mycobacterium vaccae* is a rough variant.

5. The method of claim 1, wherein the isolated non-pathogenic heat-killed *Mycobacterium vaccae* is administered to the human subject as a vaccine composition further comprising an adjuvant.

6. The method of claim 1, wherein the isolated non-pathogenic heat-killed *Mycobacterium vaccae* is administered more than once to the human subject.

7. The method of claim 1, wherein the human subject is administered from about $10^7$ to $10^9$ cells of nonpathogenic heat-killed *Mycobacterium vaccae.*

8. The method of claim 1, wherein the human subject is administered the non-pathogenic heat-killed *Mycobacterium*

*vaccae* by a route selected from the group consisting of parenteral, oral, sublingual, nasal, and pulmonary.

9. The method of claim 8, wherein the parenteral route is selected from the group consisting of subcutaneous, intradermal, subdermal, intraperitoneal, intravenous, and intravesicular injection.

10. The method of claim 9, wherein the parenteral route is subcutaneous.

* * * * *